(12) United States Patent
Li et al.

(10) Patent No.: US 10,011,631 B2
(45) Date of Patent: Jul. 3, 2018

(54) STAPLED HELICAL PEPTIDES AND METHODS OF SYNTHESIS

(71) Applicant: The University of Hong Kong, Hong Kong (HK)

(72) Inventors: Xuechen Li, Hong Kong (HK); Chi-Lung Lee, Hong Kong (HK); Jiaochao Xu, Hong Kong (HK)

(73) Assignee: The University of Hong Kong, Hong Kong (HK)

( * ) Notice: Subject to any disclaimer, the term of this patent is extended or adjusted under 35 U.S.C. 154(b) by 37 days.

(21) Appl. No.: 15/363,626

(22) Filed: Nov. 29, 2016

(65) Prior Publication Data

US 2017/0152286 A1    Jun. 1, 2017

Related U.S. Application Data

(60) Provisional application No. 62/261,395, filed on Dec. 1, 2015.

(51) Int. Cl.
| | |
|---|---|
| *A61K 38/12* | (2006.01) |
| *C07K 1/107* | (2006.01) |
| *C07K 1/12* | (2006.01) |
| *C07K 7/64* | (2006.01) |
| *C07K 14/00* | (2006.01) |
| *C07K 7/56* | (2006.01) |
| *A61K 38/00* | (2006.01) |

(52) U.S. Cl.
CPC ............ *C07K 1/1075* (2013.01); *C07K 1/122* (2013.01); *C07K 7/56* (2013.01); *C07K 7/64* (2013.01); *C07K 14/001* (2013.01); *A61K 38/00* (2013.01)

(58) Field of Classification Search
CPC .... A61K 38/00; C07K 14/001; C07K 1/1075; C07K 1/122; C07K 7/56; C07K 7/64
See application file for complete search history.

(56) References Cited

U.S. PATENT DOCUMENTS

| | | | |
|---|---|---|---|
| 7,192,713 B1 | 3/2007 | Verdine | |
| 8,859,730 B2 * | 10/2014 | Li | C07K 1/1075 |
| | | | 530/300 |
| 9,409,952 B2 * | 8/2016 | Kariyuki | C07K 1/113 |
| 9,453,044 B2 * | 9/2016 | Liu | C07K 1/02 |
| 2012/0253011 A1 * | 10/2012 | Li | C07K 1/1075 |
| | | | 530/333 |
| 2012/0270800 A1 * | 10/2012 | Verdine | C07K 1/1077 |
| | | | 514/19.4 |
| 2015/0126707 A1 * | 5/2015 | Li | C07C 227/18 |
| | | | 530/323 |
| 2015/0344519 A1 * | 12/2015 | Liu | C07K 1/02 |
| | | | 530/321 |

FOREIGN PATENT DOCUMENTS

WO     WO2017092691     *   6/2017   ............ A61K 38/16

OTHER PUBLICATIONS

Garner et al. Design and synthesis of alpha-helical peptides and mimetics. RSC Publishing, Perspective, 2007. vol. 5, pp. 3577-3585. (Year: 2007).*
Lau et al. Peptide stapling techniques based on different macrocyclisation chemistries. Chem. Soc. Rev., 2015. vol. 44, pp. 91-101. (Year: 2015).*
Lee et al. Serine/theronine ligation for the chemical synthesis of proteins. Current Opinion in Chemical Biology, 2014. vol. 22, pp. 108-114. (Year: 2014).*
Wong et al. Synthesis of Constrained Head-to-Tail Cyclic Tetrapeptides by an Imine-Induced Ring-Closing/Contraction Strategy. Angewandte Chemie, 2013, vol. 52, pp. 10212-10215. (Year: 2013).*
Blackwell, et al., "Highly Efficient Synthesis of Covalently Cross-Linked Peptide Helices by Ring-Closing Metathesis", Angew. Chem. Int. Ed., 37:3281-4 (1994).
Blackwell, et al., "Ring-closing metathesis of olefinic peptides: design, synthesis, and structural characterization of macrocyclic helical peptides", J. Org. Chem., 66(16):5291-302 (2001).
Schafmeister, et al., "An All-Hydrocarbon Cross-Linking System for Enhancing the Helicity and Metabolic Stability of Peptides", J. Am. Chem. Soc., 122:5891-2 (2000).
Sun, et al., "Membrane permeability of hydrocarbon-cross-linked peptides", Biophys. J. 104(9):1923-32 (2013).
Walensky, et al., "Activation of apoptosis in vivo by a hydrocarbon-stapled BH3 helix", Science, 305:1466-70 (2004).

* cited by examiner

*Primary Examiner* — Marcela M Cordero Garcia
(74) *Attorney, Agent, or Firm* — Pabst Patent Group LLP

(57) ABSTRACT

The present disclosure relates to the design and generation of stapled helical peptides that perturb protein-protein interactions (PPIs). The methods disclosed herein for preparing stapled peptides involve providing a peptide having a first amino acid that is functionalized with a salicylaldehyde ester side group and a second amino acid functionalized with a 1,2-hydroxyl amine side group; reacting the first and second amino acids to generate an N,O-benzylidene acetal moiety; and performing acidolysis of the resultant N,O-benzylidene acetal moiety to generate the stapled peptide. In many forms, the stapled helical peptides described herein are not hydrophobic.

20 Claims, 13 Drawing Sheets

STAPLED HELICAL PEPTIDES AND METHODS OF SYNTHESIS

CROSS-REFERENCE TO RELATED APPLICATIONS

This application claims benefit of U.S. Provisional Application No. 62/261,395, filed Dec. 1, 2015. Application No. 62/261,395, filed Dec. 1, 2015, is hereby incorporated herein by reference in its entirety.

FIELD OF THE INVENTION

The disclosed invention is generally in the field of functionalized peptides and specifically in the area of stapled helical peptides.

BACKGROUND OF THE INVENTION

Peptides are valuable and effective drugs for targeting extracellular receptors. Their use for modulating intracellular processes is hampered by their inability to enter cells, their instability, and their susceptibility to proteases. One effective strategy of stabilizing peptides involves locking them into specific, protease-resistant shapes. The α-helix is one of the major structural components of proteins and is often found at the interface of protein contacts, participating in a wide variety of intermolecular biological recognition events. However, α-helical peptides have a propensity for unraveling and forming random coils, which are, in most cases, biologically less active, or even inactive, and are highly susceptible to proteolytic degradation.

"Peptide stapling" is a term coined for a synthetic methodology used to covalently join two olefin-containing side chains present in a peptide chain using an olefin metathesis reaction (J. Org. Chem. (2001) 66(16); Blackwell et al., Angew. Chem. Int. Ed. (1994) 37:3281). Stapling of a peptide using a hydrocarbon cross-linker created from an olefin metathesis reaction has been shown to help maintain a peptide's native conformation, particularly under physiological conditions (U.S. Pat. No. 7,192,713; Schafmeister et al., J. Am. Chem. Soc. (2000) 122:5891-5892; Walensky et al., Science (2004) 305:1466-1470). A staple stabilizes a peptide in a configuration that matches the binding site of the protein target, it protects the peptide against proteolytic action, and it makes the peptide membrane permeable (Sun et al., Biophys. J. 104(9):1923-1932 (2013)). Small molecules are also cell permeable, but they are more limited in the types of targets they can bind. Stapled peptides exhibit higher specificity and affinity than small molecules, targeting intracellular control points that cannot be modulated by current therapeutics.

Protein-protein interactions (PPIs) are involved in many biological processes, hence, the discovery of molecules that perturb PPIs has led to some attractive approaches in drug discovery. PPIs involving an oft-occurring protein α-helix of 1-4 helical turns (4-15 amino acids) are promising targets, because one can design and prepare synthetic α-helix peptide ligands as the receptor antagonist. To enhance the α-helix structural stability of these short synthetic peptides in water, various covalent sidechain-to-sidechain linking strategies have been developed to stabilize the α-helical structure, including KD lactam linkers, hydrocarbon linkers, "click" triazole linkers, m-xylene thioether linkers, perfluorobenzyl thioether linkers, and alkyl thioether linkers (FIGS. 5A-5C and 5E-5G).

Each of these linkers has shown successful applications to some extent. For example, KD lactam-type peptides have been used as HIV and RSV PPI inhibitors, hydrocarbon-type peptides have been developed to promote Bcl2 apoptosis and inhibit HIV-1 capsid assembly or NOTCH transcription, and triazole-type peptides have been applied to PTH and β-catenin/Bcl9.

There are various strategies for generating stapled peptides. The main strategies involve the use of cysteine side chains for forming disulfide bridges and thioether formation (FIGS. 5D and 5H). Other methods involve ring-closing metathesis; biaryl linkage of functionalized synthetic amino acids involving borylated phenylalanine derivatives; or "click chemistry", whereby cycloaddition between an azide and a terminal or internal alkyne yields a 1,2,3-Triazole (FIG. 5C). These syntheses are expensive and laborious. Owing to the increasing interest in stapled peptides and other conformationally restricted structures, many efforts have been made to develop alternative practical and general preparative methods for their generation. Generally speaking, the above-described linkers are hydrophobic, which often causes solubility problems. Thus, improved compositions and strategies for making stapled peptides are highly desirable.

It is an object of the invention to provide stapled helical peptides with improved properties, such as higher hydrophilicity and/or greater solubility in aqueous solutions.

It is a further object of the invention to provide improved methods of preparing stapled helical peptides.

It is a further object of the invention to provide methods of treatment using stapled helical peptides.

BRIEF SUMMARY OF THE INVENTION

Described herein are strategies for the stabilization of peptides, especially flexible peptides, and most especially short, flexible peptides into well-defined conformations. Well-defined conformations are particularly valuable and useful for achieving bioactive conformations. Conformationally restricted bioactive peptides generally possess an enhanced ability to interact with proteins and other important biomolecules. The stapled peptides disclosed herein can enhance the binding affinity, proteolytic stability, and/or cellular activity of a peptide inhibitor.

Stapled helical peptides with improved properties for perturbing protein-protein interactions (PPIs) and methods for their synthesis are provided. Stapled peptides are produced by connecting two structurally optimized amino acids.

As introduced above, peptide staples can be made with linkers that are hydrophobic, which often causes solubility problems. Provided herein is an intramolecular serine/threonine ligation based method for the synthesis of stapled helical peptides. The generated stapled peptides have a β-OH lactam linker, which structurally has a chiral hydroxyl functional group, is functionally hydrophilic, and can be involved in the binding event. This peptide stapling chemistry is effective for generating bioactive peptide therapeutics.

Disclosed are staples, stapled peptides, methods of making stapled peptides, methods of using stapled peptides, and staples, peptides, compounds, and compositions for making and using the stapled peptides. Disclosed are stapled peptides wherein the staple is defined according to Formula (a) or Formula (b):

Formula (a)

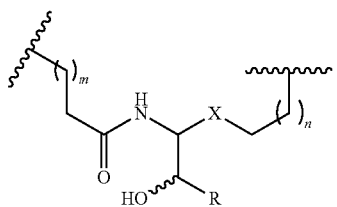

Formula (b)

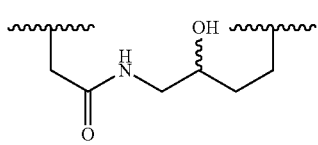

where R is H or a $C_1$-$C_{30}$ alkyl group, X is —$(CH_2)_a$— or —C(O)NH— (a is an integer from 1 to 6), m is an integer from 0 to 6, and n is an integer from 0 to 6.

Generally, the stapled peptide comprises a peptide backbone and at least one staple as described herein. In some forms, the stapled peptide can be defined according to Formula (I) or Formula (II):

Formula (I)

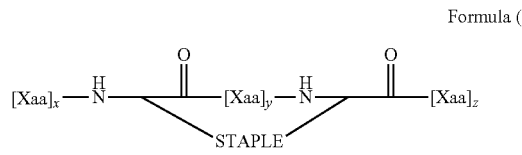

Formula (II)

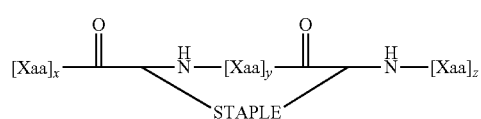

where -STAPLE- is the staple, [Xaa] is any natural or synthetic amino acid, x is an integer from 2 to 10, y is an integer from 2 to 10, and z is an integer from 2 to 10.

In some forms, the stapled peptide is water soluble. In some forms of the stapled peptide, the staple is hydrophilic. In some forms of the staple according to Formula (a), R is H. In some forms of the staple according to Formula (a), X is —$(CH_2)_a$—. In some forms of the staple according to Formula (a), X is —C(O)NH—. In some forms of the stapled peptide has a helical structure.

In some forms, the stapled peptide has one of the following structures:

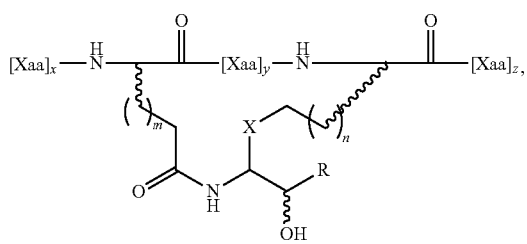

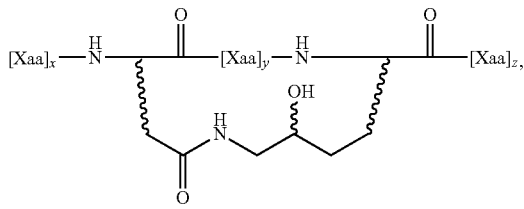

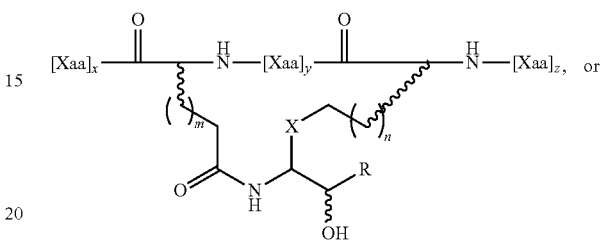

In some forms of the stapled peptides, [Xaa]y comprises the amino acid sequence of SEQ ID NO:1, SEQ ID NO:2, SEQ ID NO:3, or SEQ ID NO:4. In some forms of the stapled peptides, the linear sequence of the peptide comprises the amino acid sequence of SEQ ID NO:5, SEQ ID NO:6, SEQ ID NO:7, SEQ ID NO:8, or SEQ ID NO:9.

Also disclosed are methods for preparation of a stapled peptide. In some forms, the method comprises (a) reacting a first amino acid that is functionalized with a salicylaldehyde ester side group and a second amino acid functionalized with a 1,2-hydroxyl amine side group to generate an N,O-benzylidene acetal moiety, wherein the first amino acid and the second amino acid are comprised in a peptide; and (b) performing acidolysis of the resultant N,O-benzylidene acetal moiety to generate the stapled peptide.

In some forms, the peptide with the functionalized amino acids is defined according to Formula (III) or (IV):

Formula (III)

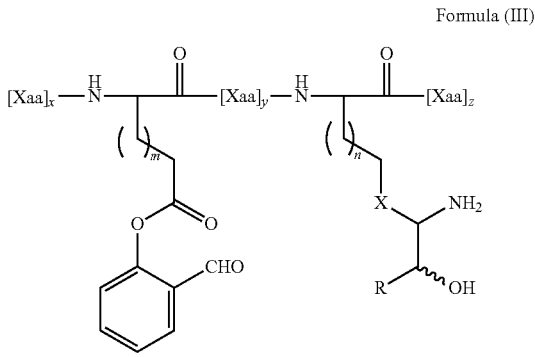

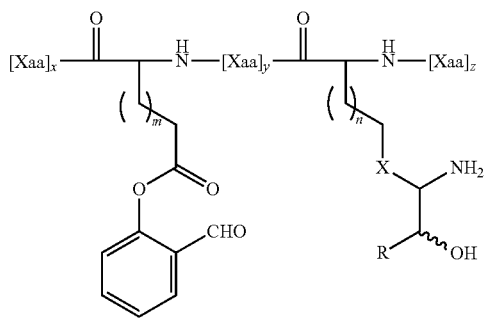

Formula (IV)

where R is H or a $C_1$-$C_{30}$ alkyl group, X is —$(CH_2)_a$— or —C(O)NH— (a is an integer from 1 to 6), m is an integer from 0 to 6, n is an integer from 0 to 6, [Xaa] is any natural or synthetic amino acid, x is an integer from 2 to 10, y is an integer from 2 to 10, and z is an integer from 2 to 10.

In some forms of the peptide according to Formula (III) or Formula (IV) (and the resultant stapled peptide), R is H. In some forms of the peptide according to Formula (III) or Formula (IV) (and the resultant stapled peptide), X is —$(CH_2)_a$—. In some forms of the peptide according to Formula (III) or Formula (IV) (and the resultant stapled peptide), X is —C(O)NH—. In some forms, the resultant stapled peptide has a helical structure.

Also disclosed are methods of treating a subject in need thereof with the disclosed stapled peptides. In some forms, the method comprises administering to the subject an effective amount of a stapled peptide as disclosed herein.

In some forms, the subject presents with a viral infection. In some forms, the infection is an HIV infection. In some forms, the infection is an RSV infection. In some forms, the stapled peptide perturbs protein-protein interactions.

In some forms, the stapled peptide has a peptide backbone and staple according to Formula (I) or Formula (II):

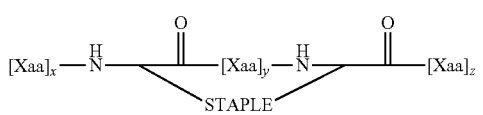

Formula (I)

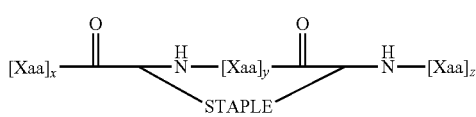

Formula (II)

where [Xaa] is any natural or synthetic amino acid, x is an integer from 2 to 10, y is an integer from 2 to 10, and z is an integer from 2 to 10. In some forms, the staple of Formula (I) or Formula (II) is defined according to Formula (a) or (b):

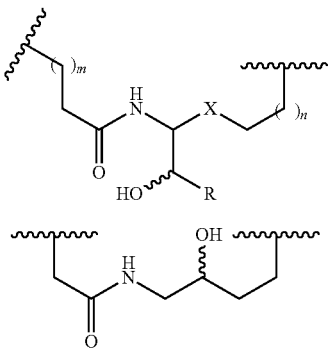

Formula (a)

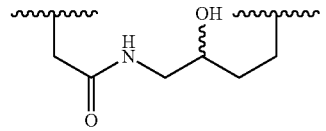

Formula (b)

where R is H or a $C_1$-$C_{30}$ alkyl group, X is —$(CH_2)_a$— and a is an integer from 1 to 6 or X is —C(O)NH—, m is an integer from 1 to 6, and n is an integer from 1 to 6.

In some forms, the stapled peptide can have one of the following structures:

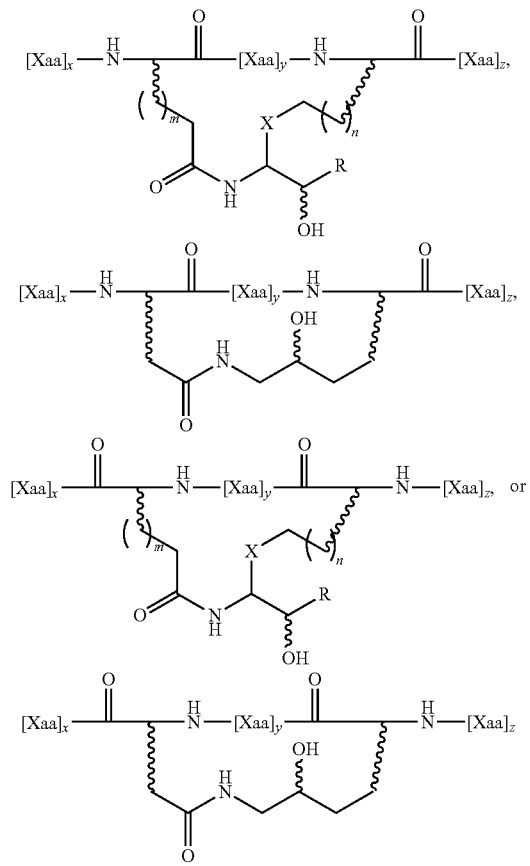

In some forms, the method for preparing stapled peptides can involve (1) providing a peptide having a first amino acid that is functionalized with a salicylaldehyde ester side group and a second amino acid functionalized with a 1,2-hydroxyl amine side group; (2) reacting the first and second amino acids to generate an N,O-benzylidene acetal moiety; and (3) performing acidolysis of the resultant N,O-benzylidene acetal moiety to generate the stapled peptide. In some forms, the peptide of step (1) can be defined according to Formula (III) or (IV):

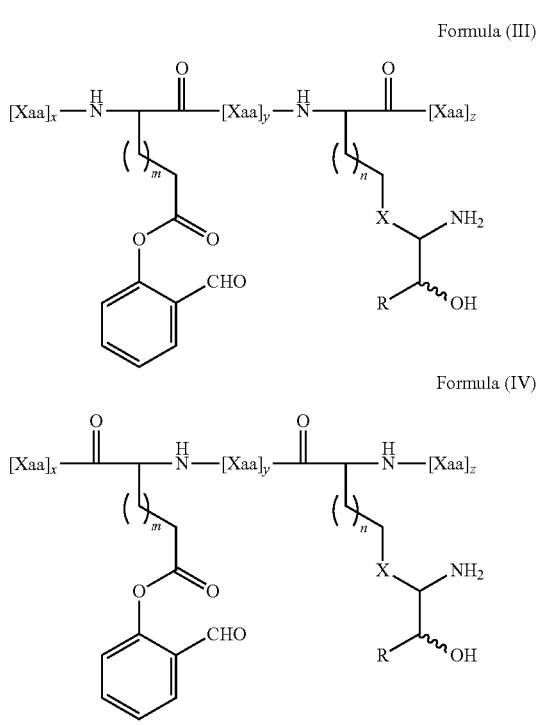

Formula (III)

Formula (IV)

where R is H or a $C_1$-$C_{30}$ alkyl group, X is a —$(CH_2)_n$— and a is an integer from 1 to 6 or X is an —CONH—, m is an integer from 1 to 6, n is an integer from 1 to 6, [Xaa] is any natural or synthetic amino acid, x is an integer from 2 to 10, y is an integer from 2 to 10, and z is an integer from 2 to 10.

The stapled helical peptides described herein can be formulated with, for example, a pharmaceutically acceptable carrier and, optionally one or more pharmaceutically acceptable excipients, for administration to a patient in need thereof.

BRIEF DESCRIPTION OF THE DRAWINGS

The accompanying drawings, which are incorporated in and constitute a part of this specification, illustrate several forms of the disclosed method and compositions and together with the description, serve to explain the principles of the disclosed method and compositions.

DETAILED DESCRIPTION OF THE INVENTION

Figure 1:
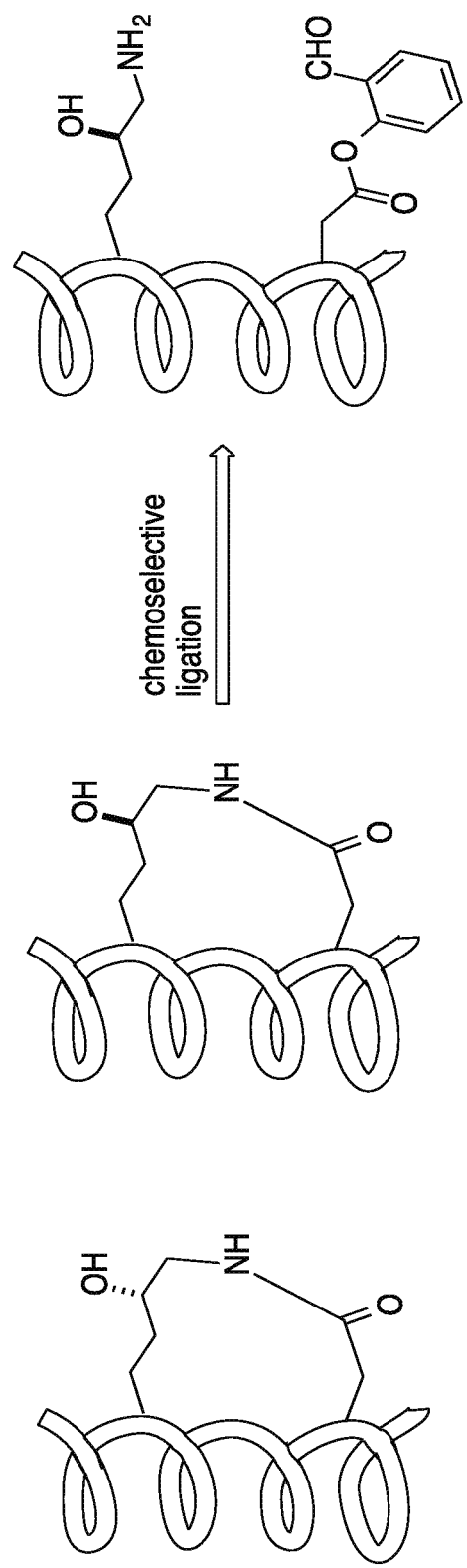
FIG. 1 is an illustration depicting exemplary stapled peptides generated using an exemplary peptide stapling strategy.

The disclosed method and compositions may be understood more readily by reference to the following detailed description of particular forms and the Examples included therein and to the Figures and their previous and following description.

I. DEFINITIONS

The term "activity" as used herein refers to a biological activity.

The terms "administer," "administering," or "administration," as used herein refers to implanting, applying, absorbing, ingesting, injecting, or inhaling, the peptide or compound.

The term "aldehyde" as used herein is represented by the formula —C(O)H.

The term "alkyl group" as used herein is a branched or unbranched saturated hydrocarbon group of 1 to 30 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is an alkyl group containing from one to six carbon atoms.

The term "amino acid" as used herein refers to a molecule containing both an amino group and a carboxyl group. Amino acids include alpha-amino acids and beta-amino acids, the structures of which are depicted below. In certain forms, an amino acid is an alpha amino acid. Amino acids can be natural or synthetic. Amino acids include, but are not limited to, the twenty standard or canonical amino acids: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V). Common non-standard or non-canonical amino acids include, but are not limited to, selenocysteine, pyrrolysine, and N-formylmethionine.

The term "carbonyl group" as used herein is represented by the formula C=O.

The term "carboxylic acid" as used herein is represented by the formula —C(O)OH.

The term "ester" as used herein is represented by the formula —C(O)OA, where A can be an alkyl, halogenated alkyl, alkenyl, alkynyl, aryl, heteroaryl, cycloalkyl, cycloalkenyl, heterocycloalkyl, or heterocycloalkenyl group described above.

The term "carbonate group" as used herein is represented by the formula —OC(O)OR, where R can be hydrogen, an alkyl, alkenyl, alkynyl, aryl, aralkyl, cycloalkyl, halogenated alkyl, or heterocycloalkyl group described above.

The term "ether" as used herein is represented by the formula $AOA^1$, where A and $A^1$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "hydrophilic" as used herein refers to the property of having a strong affinity for water; for tending to dissolve in, absorb, mix with, or be wetted by water.

The term "in need of treatment" as used herein refers to a judgment made by a caregiver (e.g. physician, nurse, nurse practitioner, or individual in the case of humans; veterinarian in the case of animals, including non-human mammals) that a subject requires or will benefit from treatment. This judgment is made based on a variety of factors that are in the realm of a care giver's expertise, but that include the knowledge that the subject is ill, or will be ill, as the result of a condition that is treatable by the compounds of the invention.

The term "isomers" as used herein includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, an isomer/enantiomer may, in some forms, be provided substantially free of the corresponding enantiomer, and may also be referred to as "optically enriched." "Optically-enriched," as used herein, means that the compound is made up of a significantly greater proportion of one enantiomer. In certain forms the compound of the present invention is made up of at least about 90% by weight of a preferred enantiomer. In other forms the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, N.Y., 1962); Wilen, S. H. Tables of Resolving Agents and Optical Resolutions p. 268 (E. L. Eliel, Ed., Univ. of Notre Dame Press, Notre Dame, Ind. 1972).

The term "linker" or "staple" as used herein refers to the cross-linker in the stapled peptide.

The term "natural amino acid" as used herein refers to both the D- and L-isomers of the 20 common naturally occurring amino acids found in peptides (e.g., A, R, N, C, D, Q, E, G, H, I, L, K, M, F, P, S, T, W, Y, V (as known by the one letter abbreviations)).

The term "peptide" as used herein refers to a class of compounds composed of amino acids chemically bound together. In general, the amino acids are chemically bound together via amide linkages (CONH); however, the amino acids may be bound together by other chemical bonds known in the art. For example, the amino acids may be bound by amine linkages. Peptide as used herein includes oligomers of amino acids and small and large peptides, including polypeptides.

The term "stapled peptide" as used herein refers to a peptide having a selected number of standard or non-standard amino acids, and further having at least two moieties capable of undergoing reaction to promote carbon-carbon bond formation, that has been contacted with a reagent to generate at least one cross-linker between the at least two moieties, which modulates, for example, peptide stability.

The term "stapling" as used herein introduces into a peptide at least two moieties capable of undergoing reaction to promote carbon-carbon bond formation that can be contacted with a reagent to generate at least one cross-linker between the at least two moieties. Stapling provides a constraint on a secondary structure, such as an α-helix structure. The length and geometry of the cross-linker can be optimized to improve the yield of the desired secondary structure content. The constraint provided can, for example, prevent the secondary structure from unfolding and/or can reinforce the shape of the secondary structure. A secondary structure that is prevented from unfolding is, for example, more stable.

The term "subject," as used herein, refers to any animal. In certain forms, the subject is a mammal. In certain forms, the term "subject", as used herein, refers to a human (e.g., a man, a woman, or a child) of either sex at any stage of development.

The term "synthetic amino acid" or "non-natural amino acid" as used herein refers to an organic compound that has a structure similar to a natural amino acid so that it mimics the structure and reactivity of a natural amino acid. The synthetic amino acid as defined herein generally increases or enhances the properties of a peptide (e.g., selectivity, stability) when the synthetic amino acid is either substituted for a natural amino acid or incorporated into a peptide.

The term "treatment" and "treating" as used herein is meant as the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, ameliorization, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

Numerical ranges disclosed in the present application of any type, disclose individually each possible number that such a range could reasonably encompass, as well as any sub-ranges and combinations of sub-ranges encompassed therein. A carbon range (i.e., $C_1$-$C_{10}$), is intended to disclose individually every possible carbon value and/or sub-range encompassed within. For example, a carbon length range of $C_1$-$C_{10}$ discloses $C_1$, $C_2$, $C_3$, $C_4$, $C_5$, $C_6$, $C_7$, $C_8$, $C_9$, and $C_{10}$, as well as discloses sub-ranges encompassed therein, such as $C_2$-$C_9$, $C_3$-$C_8$, $C_1$-$C_5$, etc.

II. STAPLED PEPTIDES

Provided herein are stapled peptides, proteins and peptides including or consisting of the stapled peptides, and pharmaceutically acceptable forms thereof. In the most preferred embodiments, the stapled peptides are stapled helical peptides. In some forms, the stapled peptides are non-helical peptides. Pharmaceutical compositions including the stapled peptide or peptides are proteins including the stapled peptides and a pharmaceutically acceptable excipient. Such pharmaceutical compositions may optionally contain one or more additional biologically active substances. For the purposes of the present disclosure, the phrase "active ingredient" generally refers to a stapled peptide, or a protein or peptide include the stapled peptide as described herein. The stapled peptide preferably has a staple linking two or more parts of a peptide backbone.

The relative amounts of the active ingredient, the pharmaceutically acceptable excipient, and/or any additional ingredients in a pharmaceutical composition will vary, depending upon the identity, size, and/or condition of the subject treated and further depending upon the route by which the composition is to be administered. By way of example, the composition may contain between 0.1% and 100% (w/w) active ingredient.

In certain forms, the stapled peptide has a peptide backbone and staple according to Formula (I) or (II):

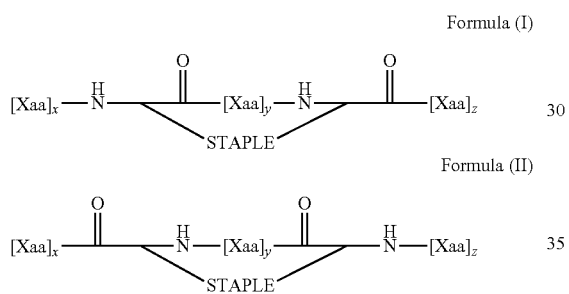

Formula (I)

Formula (II)

where [Xaa] is any natural or synthetic amino acid, x is an integer from 2 to 10, y is an integer from 2 to 10, and z is an integer from 2 to 10.

A. Peptide Backbone

The synthesis of a stapled peptide first involves the selection of a desired sequence and number of amino acids and amino acid analogues. As one of ordinary skill in the art will realize, the number, stereochemistry, and type of amino acid structures (natural or non-natural) selected will depend upon the size of the peptide to be prepared, the ability of the particular amino acids to generate a desired structural motif (e.g., an α-helix), and any particular motifs that are desirable to mimic protein domains that effectively bind to the target or effector biomolecule. In some forms, the peptides are helical. In some forms, the peptides are non-helical. Thus the stapled peptide sequence can parallel a sequence or subsequence of a known peptide or protein and improve the stability or other characteristics of an existing α-helix or other amino acid motif(s) therein. Additionally or alternatively, the stapled peptide sequence can be added to a known peptide or protein to add an α-helix or other amino acid motif(s) wherein none existed before. In some embodiments, the active agent is the stapled peptide. In some embodiments, the peptide has two or more staples. The stapled sequences can be the same or different.

In preferred embodiments, the stapled peptide includes a helical motif (i.e., a stapled helical peptide). Different amino acids have different propensities for forming different secondary structures. For example, methionine (M), alanine (A), leucine (L), glutamate (E), and lysine (K) all have especially high α-helix forming propensities. Thus in some embodiments, the stapled peptide sequence, particularly the [Xaa]y sequence, includes or consists of methionine (M), alanine (A), leucine (L), glutamate (E), and lysine (K). In contrast, proline (P) and glycine (G) are α-helix disruptors. Thus in some embodiments, the stapled peptide sequence, particularly [Xaa]y, does not include methionine (M), alanine (A), leucine (L), glutamate (E), and lysine (K).

In particular exemplary embodiments, [Xaa]y includes or consists of Ala-Arg-Arg; Glu-Tyr-Leu; Ala-Ile-Gln; Ala-Ala-Ala; Gln-Ser-Gln-Gln-Thr-Phe (SEQ ID NO:1); Asn-Leu-His-Arg-Leu Leu (SEQ ID NO:2); Gln-Asn; Glu-Asn-Pro-Glu (SEQ ID NO:3); Ile-Leu-Asp; or His-Val-Gln-Arg-Val-Leu (SEQ ID NO:4).

In exemplary embodiments, a stapled peptide includes or consists of the linear peptide sequence: Ala-Arg-Arg-Asp (salicylaldehyde ester)-Glu-Tyr-Leu-Lys(5-OH)-Ala-Ile-Gln (SEQ ID NO:5); Asp(salicylaldehyde ester)Ala-Ala-Ala-Lys(Ser) (SEQ ID NO:6); Asp(salicylaldehyde ester) Ala-Ala-Ala-Lys(5-OH) (SEQ ID NO:7); Gln-Ser-Gln-Gln-Thr-Phe-Asp(salicylaldehyde ester)-Asn-Leu-His-Arg-Leu-Leu-Lys(Ser)-Ala-Ala-Ala-Lys(Ser)-Gln-Asn (SEQ ID NO:8); or Glu-Asn-Pro-Glu-Asp(salicylaldehyde ester)-Ile-Leu-Asp-Lys(Ser)-His-Val-Gln-Arg-Val-Leu (SEQ ID NO:9). In certain forms, the peptide backbone is defined according to Formula III or IV:

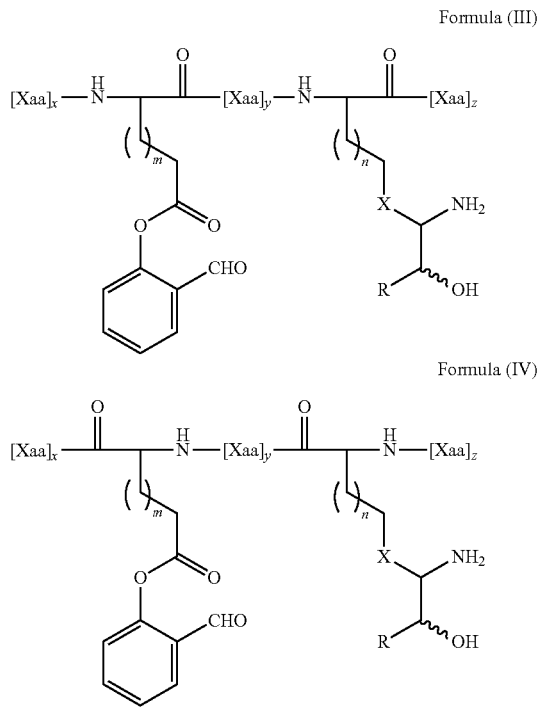

Formula (III)

Formula (IV)

where R is H or a $C_1$-$C_{30}$ alkyl group, X is a —$(CH_2)_a$— and a is an integer from 1 to 6 or X is an —CONH—, m is an integer from 0 to 6, n is an integer from 0 to 6, [Xaa] is any natural or synthetic amino acid, x is an integer from 2 to 10, y is an integer from 2 to 10, and z is an integer from 2 to 10.

It is to be understood, however, that the peptide backbone structure is not limited to above identified formulae, and, as such, may vary.

It is understood that there are numerous amino acid analogs which can be incorporated into the disclosed peptides and stapled peptides. For example, there are numerous D amino acids or other non-natural amino acids which can be used. The opposite stereoisomers of naturally occurring peptides are disclosed, as well as the stereo isomers of peptide analogs. These amino acids can readily be incorporated into polypeptide chains by chemical synthesis or by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

The peptide backbone can include any peptide or amino acid sequence that would benefit from appearing in or with a stapled peptide. For example, peptide drugs and therapeutic agents can be part of or coupled to the peptide backbone. Examples of useful peptides for this purpose include but are not limited to FORTEO®, FUZEON®, BYETTA®, corticoliberin, bivalirudin, leuprolide, secretin, thymalfasin, sermorelin.

B. Staples

In some forms, the peptides are stapled with a linker or staple that confers decreased hydrophobicity to the peptide overall, relative to another staple linker, or the combination thereof. Preferably, the generated stapled peptides have a β-OH lactam linker, which structurally has a chiral hydroxyl functional group, is functionally hydrophilic and can be involved in the binding event (see FIG. 1).

It will be appreciated that the number of crosslinking moieties (i.e. linkers or staples) is not limited to one or two, rather the number of crosslinking moieties utilized can be varied with the length of the targeting and/or effector domain as desired, and as compatible with the desired structure and activity to be generated.

In certain forms, the linkage is N-terminus to N-terminus. In certain forms, the linkage is C-terminus to N-terminus. In certain forms, the linkage is C-terminus to C-terminus. In still other forms, the linkage may be through interior amino acids of one or both peptides. As will be appreciated by one on skill in the art, the linkage is typically positioned in such a way as to avoid interfering with the binding activity of the peptide. The linkage may also be positioned in such a way to avoid interfering with the stapling of the peptide.

Figure 5A:
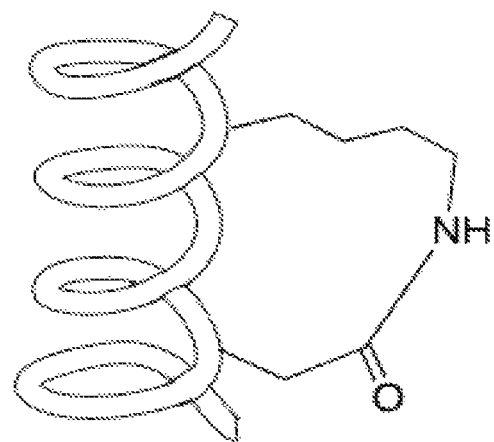
FIGS. 5A-5H are illustrations depicting known peptide stapled linkers. Shown are KD lactam (5A), hydrocarbon (5B), "Click" triazole (5C), Di-thioether (5D), m-Xylene thioether (5E), Perfluorobenzyl thioether (5F), Alkyl thioether (5G), and Di-thioether (5H) linkers.
Figure 5B:
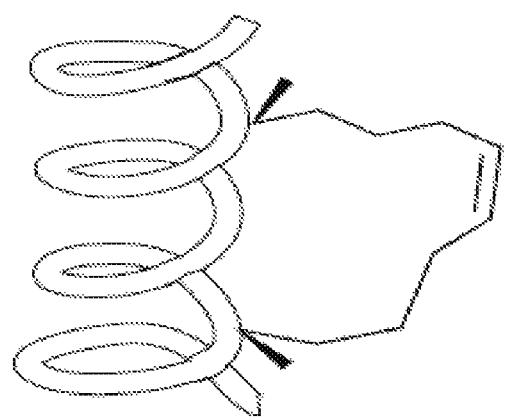
Figure 5C:
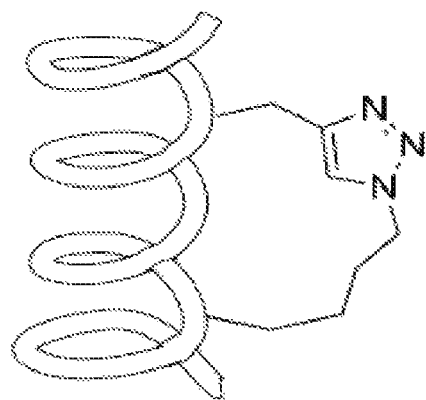
Figure 5D:
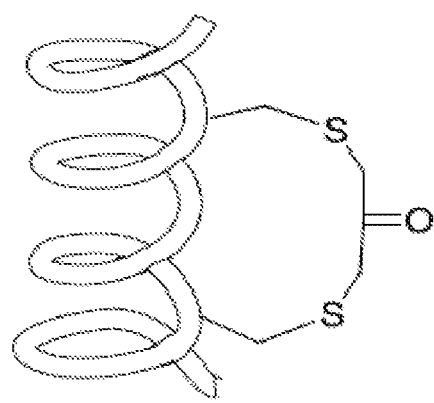
Figure 5E:
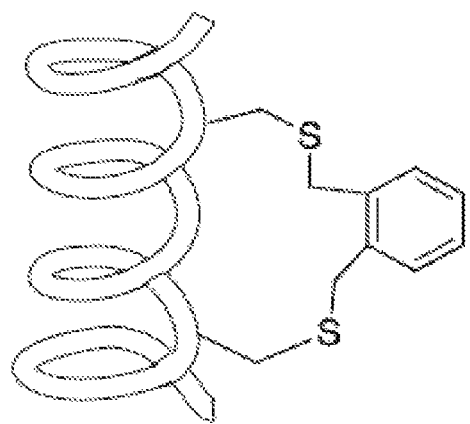
Figure 5F:
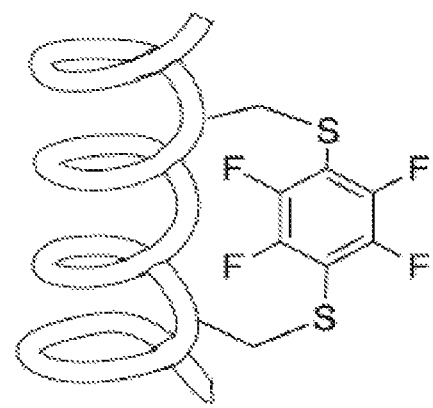
Figure 5G:
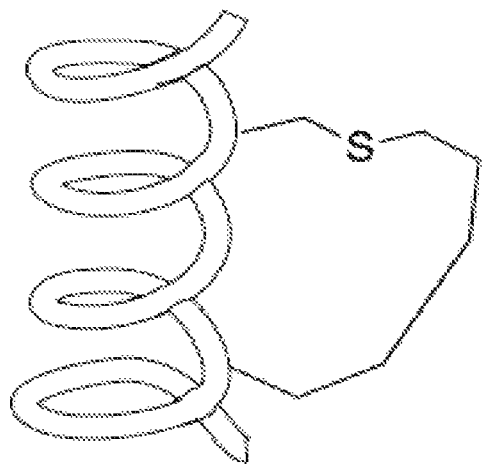
Figure 5H:
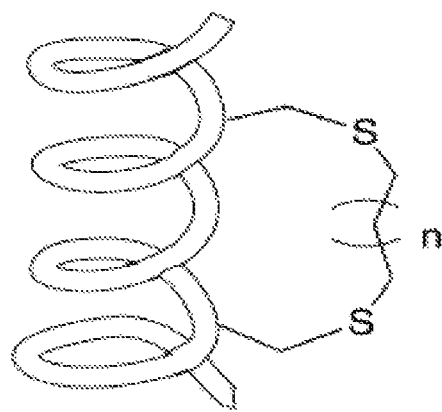
Figure 6A:
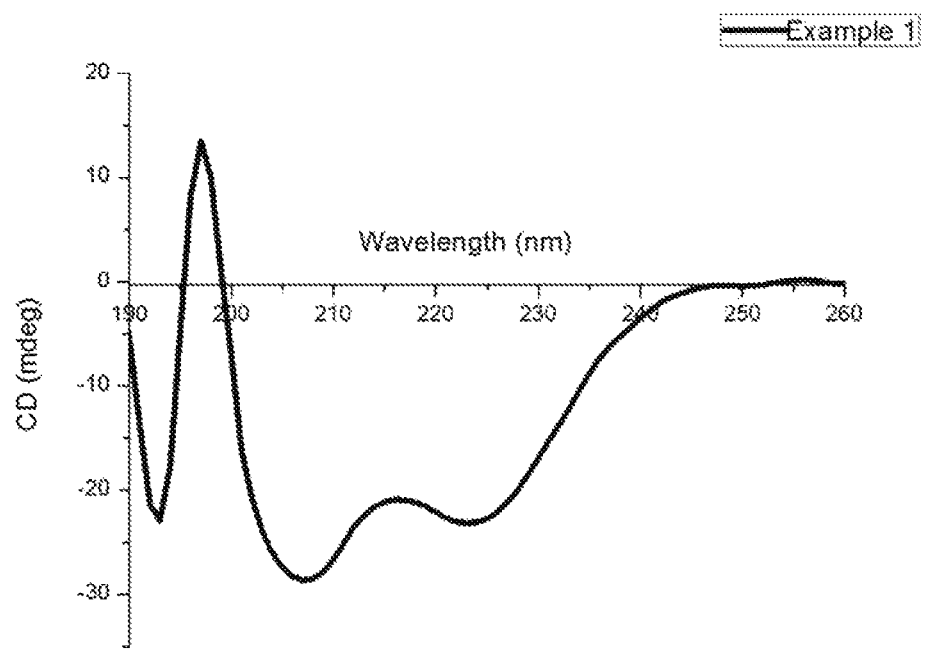
FIGS. 6A-6C are CD spectra of stapled peptides discussed in Examples 1 (6A), 3 and 4 (6B), and 5 and 6 (6C).
Figure 6B:
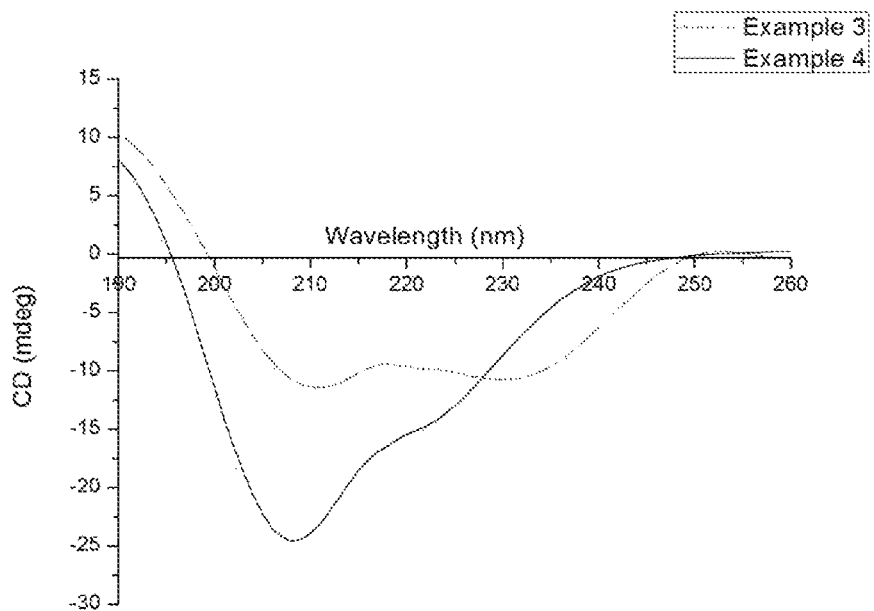
Figure 6C:
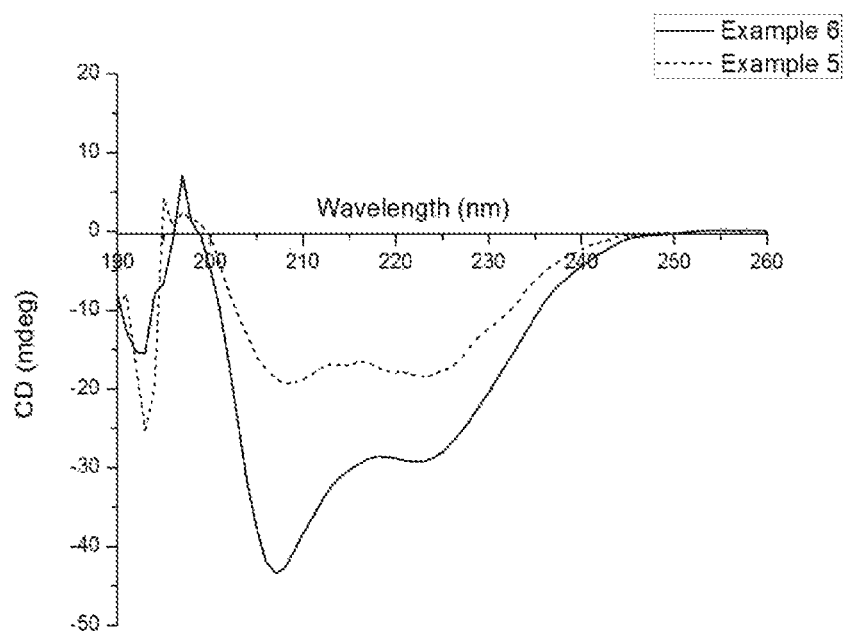

There are various strategies for generating stapled helical peptides. The main strategies involve the use of cysteine side chains for forming disulfide bridges and thioether formation (FIGS. 5D and 5H). Other methods involve ring-closing metathesis; biaryl linkage of functionalized synthetic amino acids involving borylated phenylalanine derivatives; or "click chemistry", whereby cycloaddition between an azide and a terminal or internal alkyne yields a 1,2,3-Triazole (FIG. 5C). These syntheses are expensive and laborious. The disclosed strategies and compositions offer improvements over the foregoing peptide staple technology.

Alternatives to hydrophobic hydrocarbon linkers are provided herein. For example, the staple or linker can include one or more of an ether, thioether, ester, amine, or amide moiety. In some cases, a naturally occurring amino acid side chain can be incorporated into the linker. For example, a staple or linker can be coupled with a functional group which contains a chiral hydroxyl moiety present on serine, the thiol in cysteine, the primary amine in lysine, the acid in aspartate or glutamate, or the amide in asparagine or glutamine. Accordingly, it is possible to create a staple using naturally occurring amino acids rather than using a staple that is made by coupling two non-naturally occurring amino acids. It is also possible to use a single non-naturally occurring amino acid together with a naturally occurring amino acid.

Figure 2A:
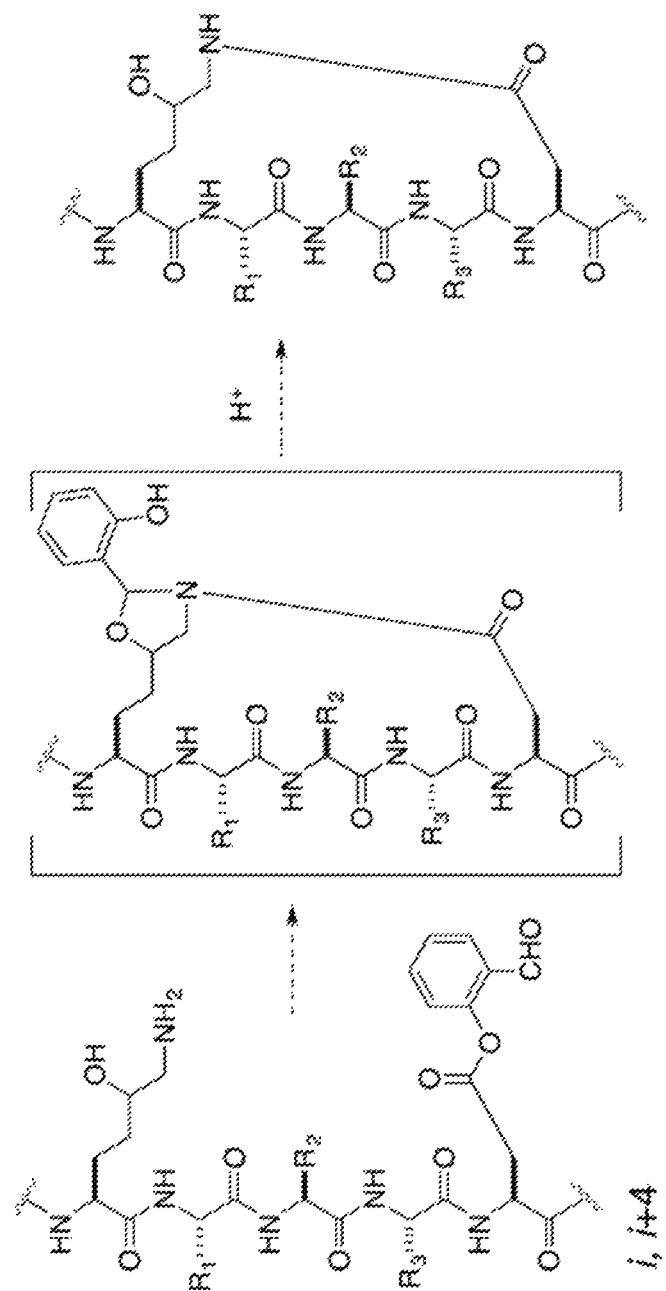
FIG. 2A is a scheme illustrating an exemplary peptide stapling strategy for peptides tethered at i and i+4 positions.
Figure 2B:
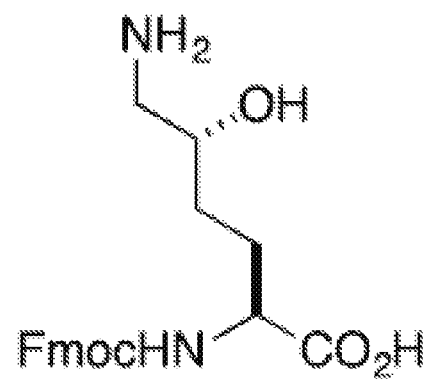
FIGS. 2B and 2C are illustrations depicting enantiomers of 5-hydroxyl lysine, which can be used as building blocks at i and i+4 positions of the peptide in FIG. 2A.
Figure 2C:
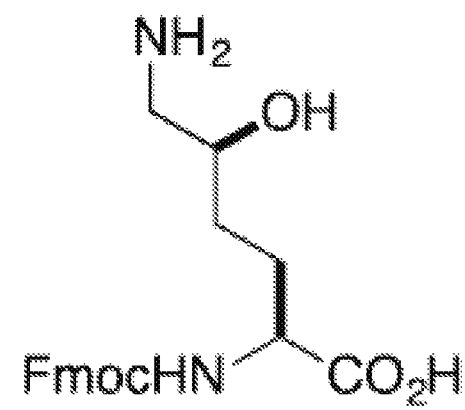

In some forms, peptides are linked using a hydrophilic linker. Some studies have revealed that a Lys-Asp (KD) lactam linker in a pentapeptide confers greater α-helicity in water, compared to a hydrocarbon linker, "click" triazole linker, m-xylene thioether linker, perfluorobenzyl thioether linker, or alkyl thioether. The synthesis of stapled peptides with a KD lactam linker involves an amide bond formation between a lysine side chain and an aspartic acid side chain at i and i+4 positions. When other lysine or aspartic acid/glutamic acid residues are present in the peptide sequence, orthogonal protection strategies are needed, which can make synthesis rather laborious. To solve this problem, 5-hydroxyl lysine (or an equivalent thereof) is used to replace lysine and a chemoselective reaction is used to synthesize K(OH)D lactam-type stapled peptides, whose synthesis can accommodate the side chain unprotected lysine and aspartic acid/glutamic acid residues present in the peptide sequence (FIG. 2A). Preferably, the K(OH)D lactam-type linker has a chiral hydroxyl group, which increases the solubility of the peptide and in some instances also facilitates engagement in the binding event.

In some forms, the staple may be defined according to Formula (a) or (b):

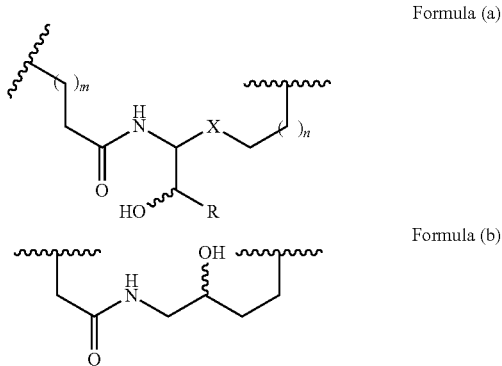

Formula (a)

Formula (b)

where R is H or a $C_1$-$C_{30}$ alkyl group, X is —$(CH_2)_a$— and a is an integer from 1 to 6 or X is —C(O)NH—, m is an integer from 0 to 6, and n is an integer from 0 to 6.

It is to be understood, however, that the staple or linker is not limited to above identified formulae, and, as such, may vary.

III. PHARMACEUTICAL COMPOSITIONS

The disclosed stapled peptides can be used to treat subjects in need thereof. For this purpose, it is useful to have the stapled peptides formulated in a pharmaceutical composition. Such pharmaceutical compositions comprise one or more of the disclosed stapled peptides and a pharmaceutically acceptable excipient.

A. Excipients

Pharmaceutical formulations of the present invention may additionally contain a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21.sup.st Edition, A. R. Gennaro, (Lippincott, Williams & Wilkins, Baltimore, Md., 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some forms, the pharmaceutically acceptable excipient is at least 95%, 96%, 97%, 98%, 99%, or 100% pure. In some forms, the excipient is approved for use in humans and for veterinary use. In some forms, the excipient is approved by the United States Food and Drug Administration. In some forms, the excipient is of pharmaceutical grade. In some forms, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the formulations. Excipients such as cocoa butter and suppository waxes, coloring agents, coating agents, sweetening, flavoring, and perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked polyvinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include, but are not limited to, natural emulsifiers {e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays {e.g. bentonite [aluminum silicate] and Veegum [magnesium aluminum silicate]), long chain amino acid derivatives, high molecular weight alcohols {e.g. stearyl alcohol, cetyl alcohol, oleyl alcohol, triacetin monostearate, ethylene glycol distearate, glyceryl monostearate, and propylene glycol monostearate, polyvinyl alcohol), carbomers {e.g., carboxy polymethylene, polyacrylic acid, acrylic acid polymer, and carboxyvinyl polymer), carrageenan, cellulosic derivatives {e.g., carboxymethylcellulose sodium, powdered cellulose, hydroxymethyl cellulose, hydroxypropyl cellulose, hydroxypropyl methylcellulose, methylcellulose), sorbitan fatty acid esters {e.g., polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g., polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g., Cremophor), polyoxyethylene ethers, (e.g., polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include, but are not limited to, starch (e.g., cornstarch and starch paste); gelatin; sugars (e.g., sucrose, glucose, dextrose, dextrin, molasses, lactose, lactitol, mannitol); natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, polyvinylpyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain forms, the preservative is an anti-oxidant. In other forms, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof. Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof. Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include, but are not limited to, pharmaceutically acceptable emulsions, microemulsions, solutions, suspensions, syrups and elixirs. In addition to the active ingredients, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain forms for parenteral administration, the conjugates of the invention are mixed with solubilizing agents such as CREMOPHOR, alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients, such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may contain buffering agents.

Solid compositions of a similar type may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient may be admixed with at least one inert diluent such as sucrose, lactose or starch. Such dosage forms may contain, as is normal practice, additional substances other than inert diluents, e.g., tableting lubricants and other tableting aids such a magnesium stearate and microcrystalline cellulose. In the case of capsules, tablets and pills, the dosage forms may contain buffering agents. They may optionally contain opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a conjugate of this invention may include ointments, pastes, creams, lotions, gels, powders, solutions, sprays, inhalants and/or patches. Generally, the active component is admixed under sterile conditions with a pharmaceutically acceptable excipient and/or any needed preservatives and/or buffers as may be required. Additionally, the present invention contemplates the use of transdermal patches, which often have the added advantage of providing controlled delivery of an active ingredient to the body. Such dosage forms may be prepared, for example, by dissolving and/or dispensing the active ingredient in the proper medium. Alternatively or additionally, the rate may be controlled by either providing a rate controlling membrane and/or by dispersing the active ingredient in a polymer matrix and/or gel.

The compounds, proteins, or peptides described herein (e.g., amino acids, and unstapled, partially stapled, and stapled peptides and proteins) may exist in particular geometric or stereoisomeric forms. They may have one or more chiral centers and thus exist as one or more stereoisomers. Such stereoisomers as encompassed by the present disclosure can exist as a single enantiomer, a mixture of diastereomers or a racemic mixture. As used herein, the term "stereoisomers" refers to compounds made up of the same atoms having the same bond order but having different three-dimensional arrangements of atoms which are not interchangeable. The three-dimensional structures are called configurations. In the present disclosure the chemical structures shown may include one or more wavy bonds therein which represent all enantiomers possible at each of the chiral centers depicted. The wavy bonds shown in chemical structures, as used herein, are intended to depict either of the chiral configurations typically depicted by hashed or wedged bonds and in peptides containing more than one wavy bond any combination of stereochemistry possible is disclosed. As used herein, the term "enantiomers" refers to two stereoisomers which are non-superimposable mirror images of one another. As used herein, the term "optical isomer" is equivalent to the term "enantiomer". As used herein the term "diastereomer" refers to two stereoisomers which are not mirror images but also not superimposable. The terms "racemate", "racemic mixture" or "racemic modification" refer to a mixture of equal parts of enantiomers. The term "chiral center" refers to a carbon atom to which four different groups are attached. Choice of the appropriate chiral column, eluent, and conditions necessary to effect separation of pairs of enantiomers is well known to one of ordinary skill in the art using standard techniques (see e.g. Jacques, J. et al., "Enantiomers, Racemates, and Resolutions", John Wiley and Sons, Inc. 1981). The present invention contemplates all such compounds, including cis- and trans-isomers, R- and S-enantiomers, diastereomers, (D)- and (L)-isomers, the racemic mixtures thereof, and other mixtures thereof, as falling within the scope of the invention.

It will be appreciated that the compounds described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include substitution with all permissible substituents of organic compounds, any of the substituents described herein (for example, aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, etc.), and any combination thereof (for example, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like) that results in the formation of a stable moiety. The present invention contemplates any and all such combinations in order to arrive at a stable substituent/moiety. Additional examples of generally applicable substituents are illustrated by the specific forms shown in the Examples, which are described herein. For purposes of this invention, heteroatoms such as nitrogen may have hydrogen substituents and/or any suitable substituent as described herein which satisfy the valencies of the heteroatoms and results in the formation of a stable moiety.

IV. METHODS OF MAKING

In some forms, the synthesis of a stapled peptide first involves the selection of a desired sequence and number of amino acids and amino acid analogues. As one of ordinary skill in the art will realize, the number, stereochemistry, and type of amino acid structures (natural or non-natural) selected will depend upon the size of the peptide to be prepared, the ability of the particular amino acids to generate a desired structural motif (e.g., an α-helix), and any particular motifs that are desirable to mimic protein domains that effectively bind to the target or effector biomolecule.

Once the amino acids are selected, synthesis of the peptide can be achieved using standard deprotection and coupling reactions. Formation of peptide bonds and polypeptide synthesis are techniques well known to one skilled in the art, and encompass both solid phase and solution phase methods; see generally, Bodanszky and Bodanszky, The Practice of Peptide Synthesis, Springer-Verlag, Berlin, 1984; Atherton and Sheppard, Solid Phase Peptide Synthesis: A Practical Approach, IRL Press at Oxford University Press Oxford, England, 1989, and Stewart and Young, Solid phase Peptide Synthesis, 2nd edition, Pierce Chemical Company, Rockford, 1984, the entire contents of each of which are incorporated herein by reference. In both solution phase and solid phase techniques, the choice of the protecting groups must be considered, as well as the specific coupling techniques to be utilized. For a detailed discussion of peptide synthesis techniques for solution phase and solid phase reactions, see, Bioorganic chemistry: Peptides and Proteins, Hecht, Oxford University Press, New York: 1998, the entire contents of which are incorporated herein by reference.

The peptides described herein, which contain at least a first amino acid therein which is functionalized with side groups such as a salicylaldehyde ester side group and a second amino acid therein which is functionalized with a 1,2-hydroxyl amine side chain can be prepared by any technique known to those skilled in the art or by techniques hereafter developed. For example, the peptides can be prepared using the solid-phase synthetic technique (Merrifield, J. Am. Chem. Soc., 15:2149-2154 (1963); M. Bodanszky et al., (1976) Peptide Synthesis, John Wiley & Sons, 2d Ed.; Kent and Clark-Lewis in Synthetic Peptides in Biology and Medicine, p. 295-358, eds. Alitalo, K., et al. Science Publishers, (Amsterdam, 1985). The synthesis of peptides by solution methods may also be used, as described in The Proteins, Vol. II, 3d Ed., p. 105-237, Neurath, H., et al., Eds., Academic Press, New York, N.Y. (1976). The synthesized peptides may be substantially purified by preparative high performance liquid chromatography or other comparable techniques available in the art. The composition of the synthetic peptides can be confirmed by any technique for amino acid composition analysis.

In some embodiments, it may be necessary to protect chemical moieties, such as hydroxyl groups. Suitable hydroxyl protecting groups are well known in the art and include those described in detail in Protecting Groups in Organic Synthesis, T. W. Greene and P. G. M. Wuts, 3rd edition, John Wiley & Sons, 1999, the entirety of which is incorporated herein by reference. Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxy ethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, .alpha.-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-climethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3- tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

In certain forms, the method involves a solution phase synthesis of a peptide. Solution phase synthesis, as mentioned above, is a well-known technique for the construction of peptides. During the course of the peptide synthesis, various parameters can be varied, including, but not limited to placement of amino acids with terminally unsaturated side chains, stereochemistry of amino acids, terminally unsaturated side chain length and functionality, and amino acid residues utilized.

Preferably, the method disclosed herein for preparing stapled peptides involves (1) providing a peptide containing a first amino acid therein that is functionalized with a salicylaldehyde ester side group and a second amino acid therein functionalized with a 1,2-hydroxyl amine side group; (2) reacting the first and second amino acids to generate an N,O-benzylidene acetal moiety; and (3) performing acidolysis of the resultant N,O-benzylidene acetal moiety to generate the stapled peptide.

Preferably, the peptide of step (1) is defined according to Formula (III) or (IV):

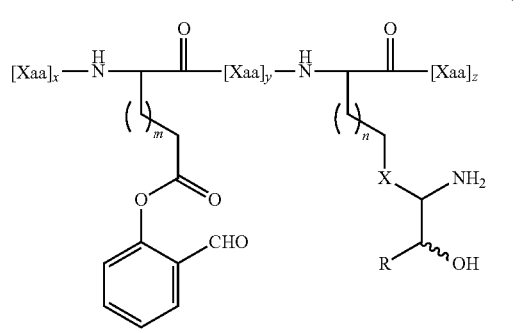

Formula (III)

Formula (IV)

where R is H or a $C_1$-$C_{30}$ alkyl group, X is a —$(CH_2)_a$— and a is an integer from 1 to 6 or X is an —CONH—, m is an integer from 0 to 6, n is an integer from 0 to 6, [Xaa] is any natural or synthetic amino acid, x is an integer from 2 to 10, y is an integer from 2 to 10, and z is an integer from 2 to 10.

In some forms, during or following step (3) the staple formed upon acidolysis is defined according to Formula (a) or (b):

Formula (a)

Formula (b)

where R is H or a $C_1$-$C_{30}$ alkyl group, X is —$(CH_2)_a$— and a is an integer from 1 to 6 or X is —C(O)NH—, m is an integer from 0 to 6, and n is an integer from 0 to 6.

In certain forms, the stapled peptide has a peptide backbone and staple according to Formula I or II:

Formula (I)

Formula (II)

where [Xaa] is any natural or synthetic amino acid, x is an integer from 2 to 10, y is an integer from 2 to 10, and z is an integer from 2 to 10.

Preferably, the stapled helical peptide has one of the following structures:

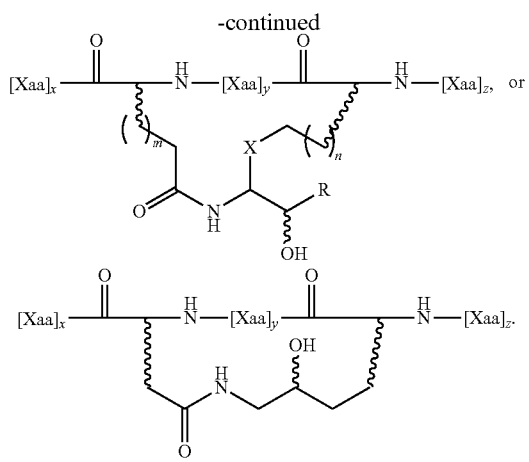

It is to be understood, however, that the stapled helical peptide structure is not limited to above identified formulae, and, as such, may vary.

Different amino acids have different propensities for forming different secondary structures. For example, methionine (M), alanine (A), leucine (L), glutamate (E), and lysine (K) all have especially high α-helix forming propensities. In contrast, proline (P) and glycine (G) are α-helix disruptors.

In certain forms, the one or more reaction steps further involve the use of a coupling reagent. Exemplary coupling reagents include, but are not limited to, benzotriazol-1-yloxy-tris(dimethylamino)-phosphonium hexafluorophosphate (BOP), benzotriazole-1-yl-oxy-tris-pyrrolidino-phosphonium hexafluorophosphate (PyBOP), bromo-tris-pyrrolidino phosphonium hexafluorophosphate (PyBroP), 1-ethyl-3-(3-dimethyllaminopropyl)carbodiimide (EDC), N,N'-carbonyldiimidazole (CDI), 3-(diethoxyphosphoryloxy)-1,2,3-benzotriazin-4(3H)-one (DEPBT), 1-hydroxy-7-azabenzotriazole (HOAt), 1-hydroxy-7-benzotriazole (HOBt), 2-(7-aza-1H-benzotriazole-1-yl)-1,1,3,3-tetramethyluronium hexafluorophosphate (HATU), 2-(6-chloro-1H-benzotriazole-1-yl)-1,1,3,3-tetramethylaminium hexafluorophosphate (HCTU), 2-(1H-benzotriazole-1-yl)-1,1,3,3-tetramethyluronium hexafluorophosphate (HBTU), O-(7-azabenzotriazole-1-yl)-N,N,N',N'-tetramethyluronium tetrafluoroborate (TATU), 2-(1H-benzotriazole-1-yl)-1,1,3,3-tetramethyluronium tetrafluoroborate (TBTU), N,N,N',N'-tetramethyl-O-(3,4-dihydro-4-oxo-1,2,3-benzotriazin-3-y-l) uranium tetrafluoroborate (TDBTU), and O—(N-succinimidyl)-1,1,3,3-tetramethyl uranium tetrafluoroborate (TSTU)).

In certain forms, the above reaction may further require a suitable base. Suitable bases include, but are not limited to, potassium carbonate, potassium hydroxide, sodium hydroxide, tetrabutylammonium hydroxide, benzyltrimethylammonium hydroxide, triethylbenzylammonium hydroxide, 1,1,3,3-tetramethylguanidine, 1,8-diazabicyclo[5.4.0]undec-7-ene (DBU), N-methylmorpholine, diisopropylethylamine (DIPEA), tetramethylethylenediamine (TMEDA), pyridine (Py), 1,4-diazabicyclo[2.2.2]octane (DABCO), N,N-dimethylamino pyridine (DMAP), or triethylamine (NEt$_3$).

In certain forms, one or more reaction steps are carried out in a suitable medium. A suitable medium is a solvent or a solvent mixture that, in combination with the combined reacting partners and reagents, facilitates the progress of the reaction there between. A suitable solvent may solubilize one or more of the reaction components, or, alternatively, the suitable solvent may facilitate the suspension of one or more of the reaction components; see generally, March's Advanced Organic Chemistry: Reactions, Mechanisms, and Structure, M. B. Smith and J. March, 5.sup.th Edition, John Wiley & Sons, 2001, and Comprehensive Organic Transformations, R. C. Larock, 2.sup.nd Edition, John Wiley & Sons, 1999, the entire contents of each of which are incorporated herein by reference. Suitable solvents for include ethers, halogenated hydrocarbons, aromatic solvents, polar aprotic solvents, or mixtures thereof. In other forms, the solvent is diethyl ether, dioxane, tetrahydrofuran (THF), dichloromethane (DCM), dichloroethane (DCE), acetonitrile (ACN), chloroform, toluene, benzene, dimethylformamide (DMF), dimethylacetamide (DMA), dimethylsulfoxide (DMSO), N-methylpyrrolidinone (NMP), or mixtures thereof.

In certain forms, one or more reaction steps are conducted at a suitable temperature, such as between about 0° C. and about 100° C.

In certain forms, the synthetic method generates one stitched product as a preferred product. As used herein a "preferred product" refers to one constitutional isomer present as the major constituent in a mixture of isomers. In certain forms, a "preferred product" refers to one constitutional isomer present as a component in at least about 50%, 55%, 60%, 65%, 70%, 75%, 80%, 85%, 90%, 95%, 98%, or 99%, of an isomeric mixture.

In some forms, stapled peptides are synthesized using intramolecular based ligation methods. This method involves the reaction of a C-terminal salicylaldehyde ester with the 1,2-hydroxylamine group to generate an NO-benzylidene acetal intermediate of step (2). Subsequently acidolysis reveals the natural peptide linkage at the ligation site. Acidolysis reaction conditions are known in the art, such as but not limited to the use of solutions of trifluoroacetic acid (TFA) or hydrogen fluoride (HF). In some other embodiments, other means of solvolysis, such as hydrolysis or alcoholysis could be employed to form the final staple from the N,O-benzylidene acetal moiety.

In some forms, 5-hydroxyl lysine (HOLys) and aspartic ester of salicylaldehyde are incorporated into the peptide as building blocks at i and i+4 positions (see FIG. 2A). Alternatively, other amino acids containing a 1,2-hydroxylamine group may be used instead of HOLys. Cyclization of the peptide into a sidechain-to-sidechain HOLys1-Asp5 lactam may be achieved by an intramolecular Ser/Thr ligation-like reaction.

Figure 3A:
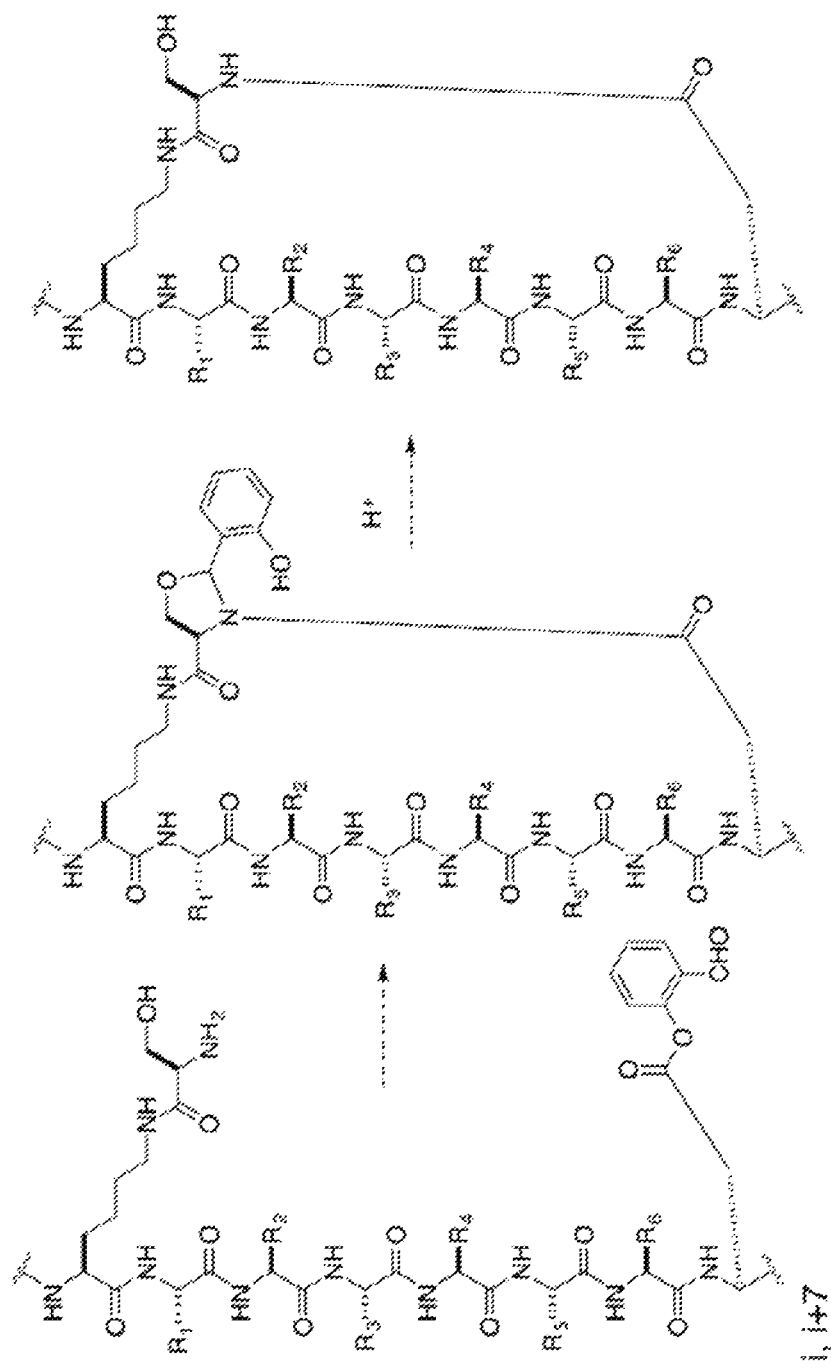
FIG. 3A is a scheme illustrating an exemplary peptide stapling strategy for peptides tethered at i and i+7 positions.
Figure 3B:
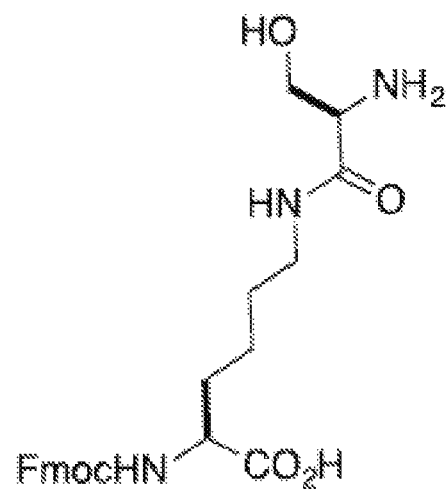
FIGS. 3B and 3C are illustrations depicting lysine-serine (3B) and lysine-5-hydroxyl lysine (3C), which can be used as building blocks at i and i+7 positions of the peptide in FIG. 3A.
Figure 3C:
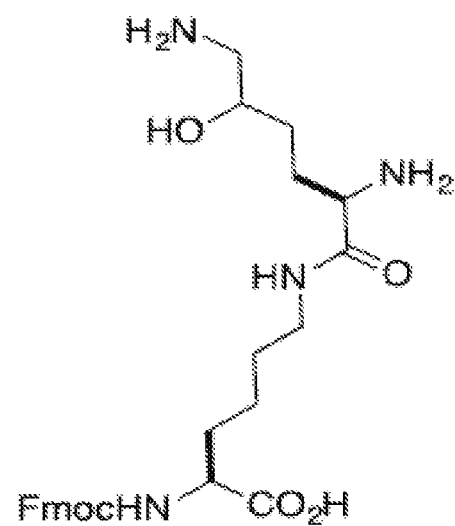
Figure 4A:
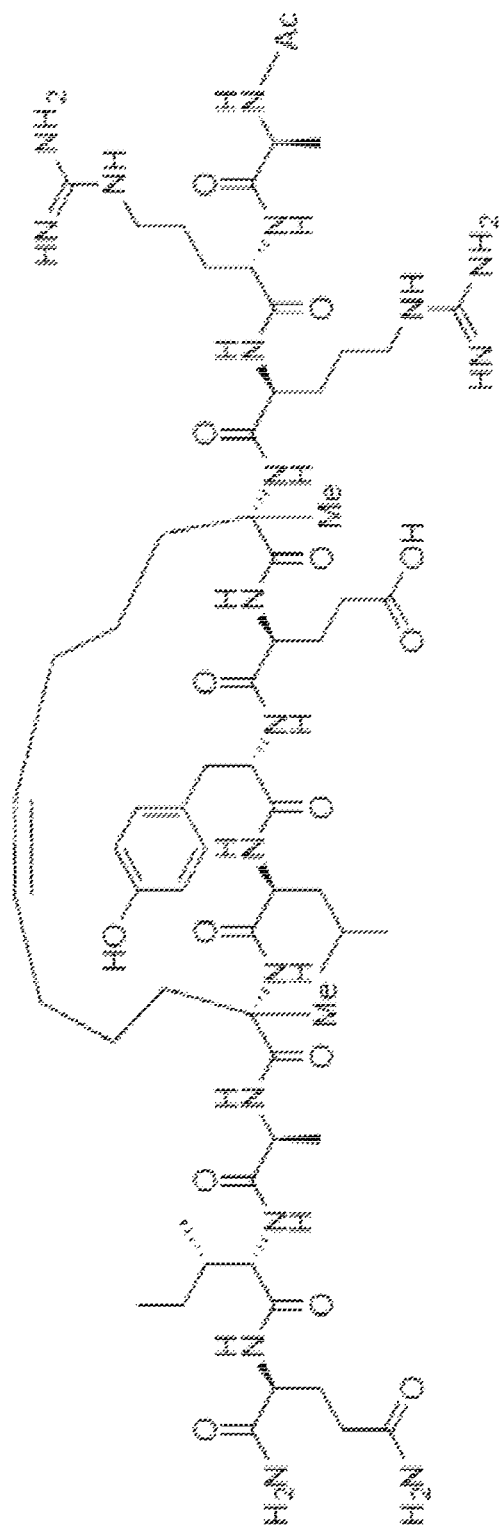
FIGS. 4A and 4B are illustrations showing a hydrocarbon linked stapled peptide (4A) and a K(OH)D lactam-type stapled peptide (4B).
Figure 4B:
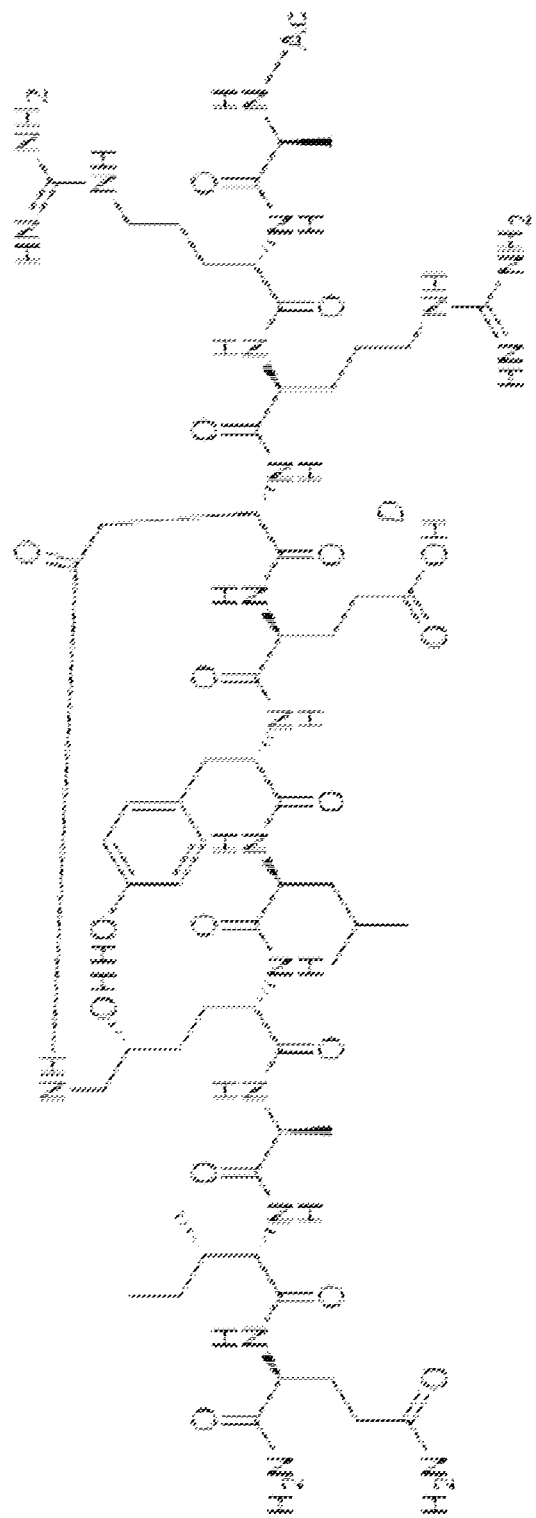

In other forms, peptides can be crosslinked at i and i+7 positions. To accommodate the longer linker necessary for crosslinking at i and i+7 positions, Lys-Ser and Lys-5-HOLys building blocks are used to replace the 5-hydroxyl lysine used in (i, i+4) stapling. The same ligation chemistry applies for sidechain-to-sidechain lactamization (see FIG. 3A).

In yet other forms, stapled peptides crosslinked at i and i+2 positions, i and i+3 positions, i and i+5 positions, i and i+6 positions, i and i+8 positions, and i and i+9 positions can be generated.

The effect of stapling on peptide secondary structure can be examined by measuring the far-UV circular dichroism (CD) spectra of the stapled peptides in water at 25° C. Generally, K(OH)D lactam-type stapled peptides exhibit higher hydrophilicity and/or greater solubility in aqueous solutions as compared to the same or similar peptide stabled according to one or more of FIGS. 5A-5H.

V. METHODS OF USE

A. Conditions

Provided are methods of treating a disease, disorder, or condition by administering to a subject diagnosed with or having susceptibility to the disease, disorder, or condition, a therapeutically effective amount of a stapled peptide. Stapled peptides, as described herein, may be useful wherever such crosslinked secondary structural motifs (particularly, a crosslinked α-helix) are advantageous, for example, as a therapeutic agent or a research tool. The stapled peptides may function as modulators of protein-protein, protein-ligand, or protein-receptor binding interactions. In certain forms, these stapled peptides are useful in the treatment of anemia, asthma, proliferative diseases, diabetes, neurological, autoimmune diseases, immunological, endocrinologic, cardiovascular, hematologic, and/or inflammatory diseases, disorders, and/or conditions, conditions characterized by premature or unwanted cell death, and conditions caused by infectious agents.

As used herein a proliferative disease, condition, or disorder includes, but is not limited to, cancer, hematopoietic neoplastic disorders, proliferative breast disease, proliferative disorders of the lung, proliferative disorders of the colon, proliferative disorders of the liver, diabetic retinopathy, and proliferative disorders of the ovary.

A wide variety of neurological diseases are characterized by the gradual loss of specific sets of neurons, and the anti-apoptotic peptides can be used in the treatment of these disorders. Such disorders include Alzheimer's disease, Parkinson's disease, amyotrophic lateral sclerosis (ALS) retinitis pigmentosa, spinal muscular atrophy, and various forms of cerebellar degeneration. The cell loss in these diseases does not induce an inflammatory response, and apoptosis appears to be the mechanism of cell death. In addition, a number of hematologic diseases are associated with a decreased production of blood cells. These disorders include anemia associated with chronic disease, aplastic anemia, chronic neutropenia, and the myelodysplastic syndromes. Disorders of blood cell production, such as myelodysplastic syndrome and some forms of aplastic anemia, are associated with increased apoptotic cell death within the bone marrow. These disorders could result from the activation of genes that promote apoptosis, acquired deficiencies in stromal cells or hematopoietic survival factors, or the direct effects of toxins and mediators of immune responses. Two common disorders associated with cell death are myocardial infarctions and stroke. In both disorders, cells within the central area of ischemia, which is produced in the event of acute loss of blood flow, appear to die rapidly as a result of necrosis. However, outside the central ischemic zone, cells die over a more protracted time period and morphologically appear to die by apoptosis. In some forms, anti-apoptotic peptides can be used to treat all such disorders associated with undesirable cell death.

Some examples of neurologic disorders that can be treated with the stapled peptides described herein include but are not limited to Alzheimer's Disease, Down's Syndrome, Dutch Type Hereditary Cerebral Hemorrhage Amyloidosis, Reactive Amyloidosis, Familial Amyloid Nephropathy with Urticaria and Deafness, Muckle-Wells Syndrome, Idiopathic Myeloma; Macroglobulinemia-Associated Myeloma, Familial Amyloid Polyneuropathy, Familial Amyloid Cardiomyopathy, Isolated Cardiac Amyloid, Systemic Senile Amyloidosis, Adult Onset Diabetes, Insulinoma, Isolated Atrial Amyloid, Medullary Carcinoma of the Thyroid, Familial Amyloidosis, Hereditary Cerebral Hemorrhage With Amyloidosis, Familial Amyloidotic Polyneuropathy, Scrapie, Creutzfeldt-Jacob disease, Gerstmann Straussler-Scheinker Syndrome, Bovine Spongiform Encephalitis, a Prion-mediated disease, Huntington's disease, Pick's disease, Amyotrophic Lateral Schlerosis (ALS), Parkinson's disease, and Lewy Body Disease.

Some examples of autoimmune diseases that can be treated with the stapled peptides described herein include but are not limited to rheumatoid arthritis, systemic lupus erythematosus, celiac disease, diabetes mellitus type 1, Graves disease, inflammatory bowel disease, multiple sclerosis, and psoriasis.

Some examples of immunological disorders that can be treated with the peptides described herein include but are not limited to organ transplant rejection, arthritis, lupus, IBD, Crohn's disease, asthma, multiple sclerosis, diabetes, Graft versus host diseases, autoimmune diseases, psoriasis, rheumatoid arthritis, etc.

Some examples of endocrinologic disorders that can be treated with the stapled helical peptides described herein include but are not limited to diabetes, hypothyroidism, hypopituitarism, hypoparathyroidism, hypogonadism, fertility disorders, etc.

Examples of cardiovascular disorders that can be treated or prevented with the peptides disclosed herein include, but are not limited to, atherosclerosis, myocardial infarction, stroke, thrombosis, aneurism, heart failure, ischemic heart disease, angina pectoris, sudden cardiac death, hypertensive heart disease; non-coronary vessel disease, such as arteriolosclerosis, small vessel disease, nephropathy, hypertriglyceridemia, hypercholesterolemia, hyperlipidemia, xanthomatosis, asthma, hypertension, emphysema and chronic pulmonary disease; or a cardiovascular condition associated with interventional procedures ("procedural vascular trauma"), such as restenosis following angioplasty, placement of a shunt, stent, synthetic or natural excision grafts, indwelling catheter, valve or other implantable devices.

Conditions caused by infectious agents that can be treated with the stapled peptides described herein may be skin infections, GI infections, urinary tract infections, genitourinary infections, systemic infections, or viral infections. In some forms the viral infection is HIV infection. In some forms, the viral infection is RSV infection.

In certain forms, stapled helical peptides can be used to alter one or more characteristics of the target. In certain forms, the characteristics of the target are altered in such a way that this alteration affects cell fate and/or cell behavior. In certain forms, changes in cell fate or cell behavior as a result of changes in one or more characteristics of the target affect the disease state of a subject, such as a mammal, for example, a human. In certain forms, stapled helical peptides can be used to treat disease. In certain forms stapled helical peptides can be used to probe or elucidate biological pathways in research. The probing of a biological pathway can be performed both in vitro such as in cell or tissue culture, or in vivo, such as in an animal, e.g., humans, mice, rats, hamsters, fish, or primates.

B. Dosage

The dosages or amounts of the compounds described herein are large enough to produce the desired effect in the method by which delivery occurs. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician based on the clinical condition of the subject involved. The dose, schedule of doses and route of administration can be varied.

The exact amount required will vary from subject to subject, depending on the species, age, and general condition of the subject, the particular protein, its mode of administration, its mode of activity, and the like. The proteins of the invention are preferably formulated in dosage unit form for ease of administration and uniformity of dosage. It will be understood, however, that the total daily usage of the proteins and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific protein employed; the specific composition employed; the age, body weight, general health, sex and diet of the patient; the time of administration, route of administration, and rate of excretion of the specific compound employed; the duration of the treatment; drugs used in combination or coincidental with the specific protein employed; and like factors well known in the medical arts.

In certain forms, the stapled peptides of the invention may be administered at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain forms, the desired dosage may be delivered using multiple administrations (e.g., two, three, four, five, six, seven, eight, nine, ten, eleven, twelve, thirteen, fourteen, or more administrations).

C. Routes of Administration

The pharmaceutical compositions of the present invention may be administered by any route. In some forms, the pharmaceutical compositions of the present invention are administered variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, buccal, enteral, sublingual; by intratracheal instillation, bronchial instillation, and/or inhalation; and/or as an oral spray, nasal spray, and/or aerosol. Specifically contemplated routes are systemic intravenous injection, regional administration via blood and/or lymph supply, and/or direct administration to an affected site. In general the most appropriate route of administration will depend upon a variety of factors including the nature of the agent (e.g., its stability in the environment of the gastrointestinal tract), the condition of the subject (e.g., whether the subject is able to tolerate oral administration), etc. At present the oral and/or nasal spray and/or aerosol route is most commonly used to deliver therapeutic agents directly to the lungs and/or respiratory system. However, the invention encompasses the delivery of the pharmaceutical composition by any appropriate route taking into consideration likely advances in the sciences of drug delivery.

The disclosed peptides and pharmaceutical compositions may be administered to animals, preferably mammals (e.g., domesticated animals, cats, dogs, mice, rats), and more preferably humans.

Liquid dosage forms for oral and parenteral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. In certain forms for parenteral administration, the proteins of the invention are mixed with solubilizing agents such Cremophor, alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

It will also be appreciated that the proteins and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, a compound may be administered concurrently with another anticancer agent), or they may achieve different effects (e.g., control of any adverse effects).

In some forms, compositions can be administered in combination with surgery to remove a tumor. Because complete removal of a tumor with minimal or no damage to the rest of a patient's body is typically the goal of cancer treatment, surgery is often performed to physically remove part or all of a tumor. If surgery is unable to completely remove a tumor, additional therapies (e.g., chemotherapy, radiation therapy, hormonal therapy, immunotherapy, complementary or alternative therapy) may be employed. In some forms, compositions can be administered in combination with radiation therapy. Radiation therapy (also known as radiotherapy, X-ray therapy, or irradiation) is the use of ionizing radiation to kill cancer cells and shrink tumors. Radiation therapy may be used to treat almost any type of solid tumor, including cancers of the brain, breast, cervix, larynx, lung, pancreas, prostate, skin, stomach, uterus, or soft tissue sarcomas. Radiation can be used to treat leukemia and lymphoma. Radiation therapy can be administered externally via external beam radiotherapy (EBRT) or internally via brachytherapy. Typically, the effects of radiation therapy are localized and confined to the region being treated. Radiation therapy injures or destroys tumor cells in an area being treated (e.g., a target organ, tissue, and/or cell) by damaging their genetic material, preventing tumor cells from growing and dividing. In general, radiation therapy attempts to damage as many tumor cells as possible while limiting harm to nearby healthy tissue. Hence, it is often administered in multiple doses, allowing healthy tissue to recover between fractions.

In some forms, compositions can be administered in combination with immunotherapy. Immunotherapy is the use of immune mechanisms against tumors which can be used in various forms of cancer, such as breast cancer (e.g., trastuzumab/HERCEPTIN®), leukemia (e.g., gemtuzumab ozogamicin/MYLOTARG®), and non-Hodgkin's lymphoma (e.g., rituximab/RITUXAN®). In some forms, immunotherapy agents are monoclonal antibodies directed against proteins that are characteristic to the cells of the cancer in question. In some forms, immunotherapy agents are cytokines that modulate the immune system's response. In some forms, immunotherapy agents may be vaccines.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

EXAMPLES

Example 1: Synthesis of Ala-Arg-Arg-Asp(Salicylaldehyde Ester)-Glu-Tyr-Leu-Lys(5-OH)-Ala-Ile-Gln Stapled Peptide Linear peptide Ala-Arg-Arg-Asp(salicylaldehyde ester)-Glu-Tyr-Leu-Lys(5-OH)-Ala-Ile-Gln (SEQ ID NO:5) was synthesized by following a standard 9H-fluoren-9-yl-methoxycarbonyl (Fmoc) solid phase peptide synthesis protocol on a Rink-amide resin. Briefly, three equiv. of HATU, three equiv. of amino acids, and six equiv. of DIEA in DMF were used in each coupling reaction. The coupling reaction was allowed to proceed for 40 minutes. Fmoc deprotection was accomplished by treating the resin-bound peptides with 20% piperidine/DMF (2×, 10 min each). The peptides were cleaved from the Rink amide resin by treating the resin with a cleavage cocktail containing 95% TFA and 2.5% water for 1 hour. The filtrates were concentrated. The crude peptides were dissolved in pyridine/acetic acid buffer (mole:mole, 1:2) at an estimated concentration (based on the resin loading) of 5 mM in a flask at room temperature for 1 hour. The solution was concentrated, and then treated with a cocktail containing 95% TFA and 2.5% water for 10 min. The crude product was purified by preparative RP-HPLC to give an i, i+4 stapled peptide (6 mg, 35% based on the resin loading).

Example 2: Evaluation of Solubility

To examine the solubility performance of this stapled peptide compared to commonly used hydrocarbon linked stapled peptides, the solubility of compound 1 (Ala-Arg-Arg-S5-Glu-Tyr-Leu-S5-Ala-Ile-Gln (SEQ ID NO:10) and K(OH)D lactam-typed stapled peptide (2) was assessed. Hydrocarbon linked stapled peptides have very poor solubility in water, which results in no binding affinity to the MAGUK GK domain. The K(OH)D lactam-type stapled peptide exhibited very good solubility and the binding affinity with the GK domain was 5.9 μM from ITC studies.

Example 3: Synthesis of Asp(Salicylaldehyde Ester)Ala-Ala-Ala-Lys(Ser) Stapled Peptide Linear peptide Asp(salicylaldehyde ester)Ala-Ala-Ala-Lys(Ser) (SEQ ID NO:6) was synthesized by following a standard 9H-fluoren-9-yl-methoxycarbonyl (Fmoc) solid phase peptide synthesis protocol on a Rink-amide resin. Briefly, three equiv. of HATU, three equiv. of amino acids, and six equiv. of DIEA in DMF were used in each coupling reaction. The coupling reaction was allowed to proceed for 40 minutes. Fmoc deprotection was accomplished by treating the resin-bound peptides with 20% piperidine/DMF (2×, 10 min each). The peptides were cleaved from the Rink amide resin by treating the resin with a cleavage cocktail containing 95% TFA and 2.5% water for 1 hour. The filtrates were concentrated. The crude peptides were dissolved in pyridine/acetic acid buffer (mole:mole, 1:2) at an estimated concentration (based on the resin loading) of 5 mM in a flask at room temperature for 1 hour. The solution was concentrated, and then treated with a cocktail containing 95% TFA and 2.5% water for 10 min. The crude product was purified by preparative RP-HPLC to give an i, i+4 stapled peptide (12 mg, 42% based on the resin loading).

Example 4: Synthesis of Asp(Salicylaldehyde Ester)Ala-Ala-Ala-Lys(5-OH) Stapled Peptide Linear peptide Asp(salicylaldehyde ester)Ala-Ala-Ala-Lys(5-OR) (SEQ ID NO:7) was synthesized by following a standard 9H-fluoren-9-yl-methoxycarbonyl (Fmoc) solid phase peptide synthesis protocol on a Rink-amide resin. Briefly, three equiv. of HATU, three equiv. of amino acids, and six equiv. of DIEA in DMF were used in each coupling reaction. The coupling reaction was allowed to proceed for 40 minutes. Fmoc deprotection was accomplished by treating the resin-bound peptides with 20% piperidine/DMF (2×, 10 min each). The peptides were cleaved from the Rink amide resin by treating the resin with a cleavage cocktail containing 95% TFA and 2.5% water for 1 hour. The filtrates were concentrated. The crude peptides were dissolved in pyridine/acetic acid buffer (mole:mole, 1:2) at an estimated concentration (based on the resin loading) of 5 mM in a flask at a room temperature for 1 hour. The solution was concentrated, and then treated with a cocktail containing 95% TFA and 2.5% water for 10 min. The crude product was purified by preparative RP-HPLC to give an i, i+4 stapled peptide (5 mg, 30% based on the resin loading).

Example 5: Synthesis of Gln-Ser-Gln-Gln-Thr-Phe-Asp(Salicylaldehyde Ester)-Asn-Leu-his-Arg-Leu-Leu-Lys(Ser)-Ala-Ala-Ala-Lys(Ser)-Gln-Asn Stapled Peptide Linear peptide Gln-Ser-Gln-Gln-Thr-Phe-Asp(salicylaldehyde ester)-Asn-Leu-His-Arg-Leu-Leu-Lys(Ser)-Ala-Ala-Ala-Lys(Ser)-Gln-Asn (SEQ ID NO:8) was synthesized by following a standard 9H-fluoren-9-yl-methoxycarbonyl (Fmoc) solid phase peptide synthesis protocol on a Rink-amide resin. Briefly, three equiv. of HATU, three equiv. of amino acids, and six equiv. of DIEA in DMF were used in each coupling reaction. The coupling reaction was allowed to proceed for 40 minutes. Fmoc deprotection was accomplished by treating the resin-bound peptides with 20% piperidine/DMF (2×, 10 min each). The peptides were cleaved from the Rink amide resin by treating the resin with a cleavage cocktail containing 95% TFA and 2.5% water for 1 hour. The filtrates were concentrated. The crude peptides were dissolved in pyridine/acetic acid buffer (mole:mole, 1:2) at an estimated concentration (based on the resin loading) of 5 mM in a flask at room temperature for 1 hour. The solution was concentrated, and then treated with a cocktail containing 95% TFA and 2.5% water for 10 min. The crude product was purified by preparative RP-HPLC to give an i, i+7 stapled peptide (10 mg, 40% based on the resin loading).

Example 6: Synthesis of Glu-Asn-Pro-Glu-Asp(Salicylaldehyde Ester)-Ile-Leu-Asp-Lys(Ser)-his-Val-Gln-Arg-Val-Leu Stapled Peptide Linear peptide Glu-Asn-Pro-Glu-Asp(salicylaldehyde ester)-Ile-Leu-Asp-Lys(Ser)-His-Val-Gln-Arg-Val-Leu (SEQ ID NO:9) was synthesized by following a standard 9H-fluoren-9-yl-methoxycarbonyl (Fmoc) solid phase peptide synthesis protocol on a Rink-amide resin. Briefly, three equiv. of HATU, three equiv. of amino acids, and six equiv. of DIEA in DMF were used in each coupling reaction. The coupling reaction was allowed to proceed for 40 minutes. Fmoc deprotection was accomplished by treating the resin-bound peptides with 20% piperidine/DMF (2×, 10 min each). The peptides were cleaved from the Rink amide resin by treating the resin with a cleavage cocktail containing 95% TFA and 2.5% water for 1 hour. The filtrates were concentrated. The crude peptides were dissolved in pyridine/acetic acid buffer (mole:mole, 1:2) at an estimated concentration (based on the resin loading) of 5 mM in a flask at room temperature for 1 hour. The solution was concentrated, and then treated with a cocktail containing 95% TFA and 2.5% water for 10 min. The crude product was purified by preparative RP-HPLC to give an i, i+4 stapled peptide (13 mg, 45% based on the resin loading).

Those skilled in the art will recognize, or be able to ascertain using no more than routine experimentation, many equivalents to the specific forms of the method and compositions described herein. Such equivalents are intended to be encompassed by the following claims.

We claim:

1. A stapled peptide, wherein the stapled peptide comprises a peptide backbone and at least one staple, wherein the stapled peptide is defined according to Formula (I) or Formula (II):

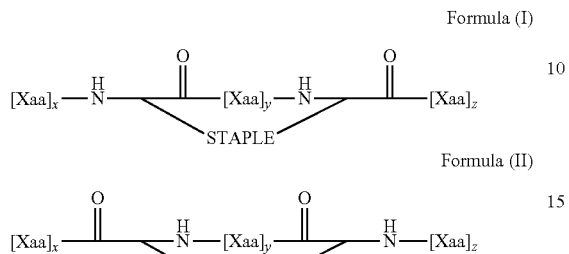

Formula (I)

Formula (II)

wherein:
[Xaa] is any natural or synthetic amino acid;
x is an integer from 2 to 10;
y is an integer from 2 to 10; and
z is an integer from 2 to 10, wherein:
the staple is defined according to Formula (a) or Formula (b):

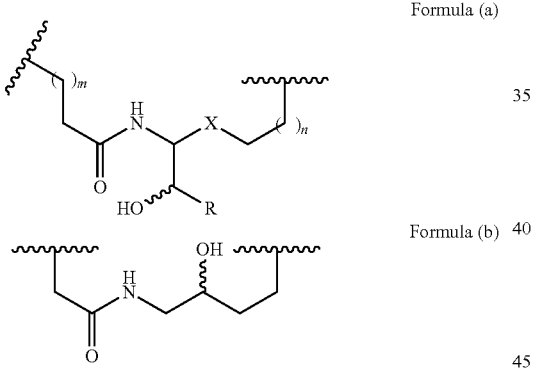

Formula (a)

Formula (b)

wherein:
R is H or a $C_1$-$C_{30}$ alkyl group;
X is —$(CH_2)_a$— or —C(O)NH—, wherein a is an integer from 1 to 6;
m is an integer from 0 to 6; and
n is an integer from 0 to 6.

2. The stapled peptide of claim 1, wherein the staple is hydrophilic.

3. The stapled peptide of claim 1, wherein for the staple according to Formula (a) R is H.

4. The stapled peptide of claim 1, wherein for the staple according to Formula (a) X is —$(CH_2)_a$—.

5. The stapled peptide of claim 1, wherein for the staple according to Formula (a) X is —C(O)NH—.

6. The stapled peptide of claim 1, wherein the stapled peptide has a helical structure.

7. The stapled peptide of claim 1, wherein the stapled peptide has one of the following structures:

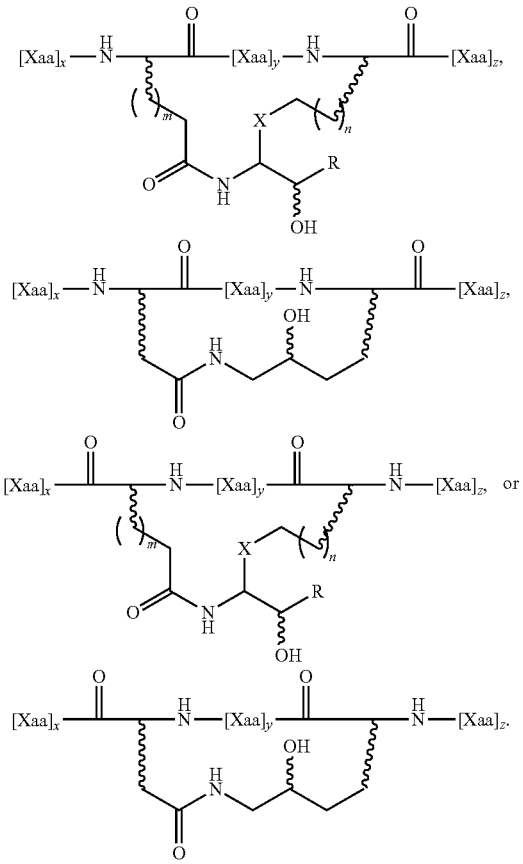

8. The stapled peptide of claim 1, wherein the stapled peptide is water soluble.

9. A method for preparation of a stapled peptide, the method comprising:
(a) reacting a first amino acid that is functionalized with a salicylaldehyde ester side group and a second amino acid functionalized with a 1,2-hydroxyl amine side group to generate an N,O-benzylidene acetal moiety, wherein the first amino acid and the second amino acid are comprised in a peptide; and
(b) performing acidolysis of the resultant N,O-benzylidene acetal moiety to generate the stapled peptide.

10. The method of claim 9, wherein the peptide is defined according to Formula (III) or (IV):

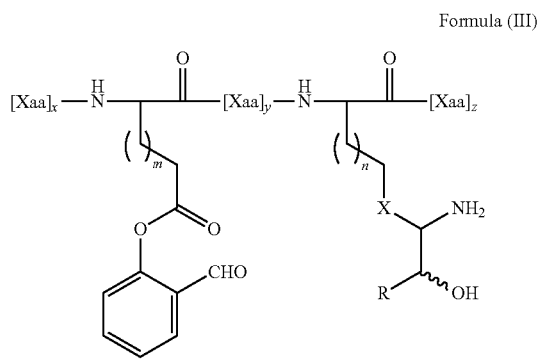

Formula (III)

-continued

Formula (IV)

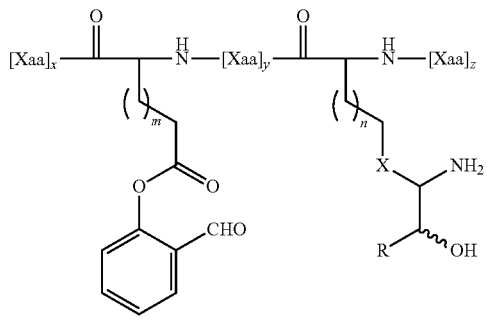

wherein:
R is H or a $C_1$-$C_{30}$ alkyl group;
X is —$(CH_2)_a$— or —C(O)NH—, wherein a is an integer from 1 to 6;
m is an integer from 0 to 6;
n is an integer from 0 to 6;
[Xaa] is any natural or synthetic amino acid;
x is an integer from 2 to 10;
y is an integer from 2 to 10; and
z is an integer from 2 to 10.

11. The method of claim 10, wherein for the peptide according to Formula (III) or Formula (IV) R is H.

12. The method of claim 10, wherein for the peptide according to Formula (III) or Formula (IV) X is —$(CH_2)_a$—.

13. The method of claim 10, wherein for the peptide according to Formula (III) or Formula (IV) X is —C(O)NH—.

14. The method of claim 10, wherein the stapled peptide has a helical structure.

15. A method of treating a subject in need thereof, the method comprising administering to the subject an effective amount of a stapled peptide according to claim 1.

16. The method of claim 15, wherein the subject presents with a viral infection.

17. The method of claim 16, wherein the infection is an HIV infection.

18. The method of claim 16, wherein the infection is an RSV infection.

19. The method of claim 16, wherein the stapled peptide perturbs protein-protein interactions.

20. The method of claim 16, wherein (a) [Xaa]y comprises the amino acid sequence of SEQ ID NO:1, SEQ ID NO:2, SEQ ID NO:3, or SEQ ID NO:4; or (b) the linear sequence of the peptide comprises the amino acid sequence of SEQ ID NO:5, SEQ ID NO:6, SEQ ID NO:7, SEQ ID NO:8, or SEQ ID NO:9.

* * * * *

SEQUENCE LISTING

```
<160> NUMBER OF SEQ ID NOS: 10

<210> SEQ ID NO 1
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 1

Gln Ser Gln Gln Thr Phe
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 2

Asn Leu His Arg Leu Leu
1               5

<210> SEQ ID NO 3
<211> LENGTH: 4
<212> TYPE: PRT
<213> ORGANISM: Artificial Sequence
```

```
<220> FEATURE:
<223> OTHER INFORMATION: Synthetic Peptide

<400> SEQUENCE: 3

Gln Asn Pro Glu
1

<210> SEQ ID NO 4
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 4

His Val Gln Arg Val Leu
1               5

<210> SEQ ID NO 5
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: Salicylaldehyde ester modification
<220> FEATURE:
<221> NAME/KEY: MISC_FEATURE
<222> LOCATION: (8)..(8)
<223> OTHER INFORMATION: Lysine is modified with a 5' Hydroxyl

<400> SEQUENCE: 5

Ala Arg Arg Asp Glu Tyr Leu Lys Ala Ile Gln
1               5                   10

<210> SEQ ID NO 6
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Salicylaldehyde ester modification
<220> FEATURE:
<221> NAME/KEY: MISC_FEATURE
<222> LOCATION: (5)..(5)
<223> OTHER INFORMATION: Lysine-Serine modification

<400> SEQUENCE: 6

Asp Ala Ala Ala Lys
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Salicylaldehyde ester modification
<220> FEATURE:
<221> NAME/KEY: MISC_FEATURE
<222> LOCATION: (5)..(5)
<223> OTHER INFORMATION: 5' Hydroxyl modification
```

```
<400> SEQUENCE: 7

Asp Ala Ala Ala Lys
1               5

<210> SEQ ID NO 8
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (7)..(7)
<223> OTHER INFORMATION: Salicylaldehyde ester modification
<220> FEATURE:
<221> NAME/KEY: MISC_FEATURE
<222> LOCATION: (14)..(14)
<223> OTHER INFORMATION: Lysine-Serine modification
<220> FEATURE:
<221> NAME/KEY: MISC_FEATURE
<222> LOCATION: (18)..(18)
<223> OTHER INFORMATION: Lysine-Serine modification

<400> SEQUENCE: 8

Gln Ser Gln Gln Thr Phe Asp Asn Leu His Arg Leu Leu Lys Ala Ala
1               5                   10                  15

Ala Lys Gln Asn
            20

<210> SEQ ID NO 9
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: Salicylaldehyde ester modification
<220> FEATURE:
<221> NAME/KEY: MISC_FEATURE
<222> LOCATION: (9)..(9)
<223> OTHER INFORMATION: Lysine-Serine modification

<400> SEQUENCE: 9

Glu Asn Pro Glu Asp Ile Leu Asp Lys His Val Gln Arg Val Leu
1               5                   10                  15

<210> SEQ ID NO 10
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: S absolute configuration at the C-alpha carbon;
      the number of C atoms being 5 in the alkenyl side chain.
<220> FEATURE:
<221> NAME/KEY: MISC_FEATURE
<222> LOCATION: (6)..(6)
<223> OTHER INFORMATION: S absolute configuration at the C-alpha carbon;
      the number of C atoms being 5 in the alkenyl side chain.

<400> SEQUENCE: 10

Ala Ala Arg Glu Tyr Leu Ala Ile Gln
1               5
```